(12) United States Patent
Dowell et al.

(10) Patent No.: US 10,073,090 B2
(45) Date of Patent: Sep. 11, 2018

(54) ASSAY WITH INCREASED DYNAMIC RANGE

(71) Applicant: ABBOTT LABORATORIES, Abbott Park, IL (US)

(72) Inventors: Barry L. Dowell, Mundelein, IL (US); Susan Gayda, Gurnee, IL (US); Qiaoqiao Ruan, Kildeer, IL (US); Joseph P. Skinner, Lake Villa, IL (US); Sergey Y. Tetin, Lindenhurst, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/842,834

(22) Filed: Sep. 2, 2015

(65) Prior Publication Data
US 2016/0054317 A1   Feb. 25, 2016

Related U.S. Application Data

(62) Division of application No. 13/833,655, filed on Mar. 15, 2013, now Pat. No. 9,157,910.

(51) Int. Cl.
*G01N 33/53* (2006.01)
*G01N 33/543* (2006.01)

(52) U.S. Cl.
CPC ... *G01N 33/54393* (2013.01); *G01N 33/5306* (2013.01); *G01N 33/54306* (2013.01)

(58) Field of Classification Search
None
See application file for complete search history.

(56) References Cited

U.S. PATENT DOCUMENTS

| | | |
|---|---|---|
| 4,595,611 A | 6/1986 | Cragle et al. |
| 4,595,661 A | 6/1986 | Cragle et al. |
| 5,006,309 A | 4/1991 | Khalil et al. |
| 5,063,081 A | 11/1991 | Cozzette et al. |
| 5,089,424 A | 2/1992 | Khalil et al. |
| 5,242,828 A | 9/1993 | Bergstrom et al. |
| 5,260,203 A | 11/1993 | Ladner et al. |
| 5,294,404 A | 3/1994 | Grandone et al. |
| 5,352,803 A | 10/1994 | Mattingly |
| 5,359,093 A | 10/1994 | Adamczyk et al. |
| 5,470,956 A * | 11/1995 | Hayashi .............. C07K 16/18 530/388.9 |
| 5,496,925 A | 3/1996 | Mattingly |
| 5,573,904 A | 11/1996 | Mattingly |
| 5,585,241 A | 12/1996 | Lindmo |
| 5,593,896 A | 1/1997 | Adamczyk et al. |
| 5,770,380 A | 6/1998 | Hamilton et al. |
| 6,184,042 B1 | 2/2001 | Neumann |
| 6,225,047 B1 | 5/2001 | Hutchens et al. |
| 6,329,209 B1 | 12/2001 | Wagner et al. |
| 6,350,579 B1 | 2/2002 | Nelson |
| 6,818,418 B1 | 11/2004 | Lipovsek et al. |
| 7,115,396 B2 | 10/2006 | Lipovsek et al. |
| 7,501,287 B2 | 3/2009 | Orning |
| 8,192,943 B2 | 6/2012 | Harris et al. |
| 9,005,901 B2 | 4/2015 | Gayda et al. |
| 9,157,910 B2 | 10/2015 | Dowell et al. |
| 2003/0148542 A1 | 8/2003 | Pawlak et al. |
| 2003/0170881 A1 | 9/2003 | Davis et al. |
| 2004/0018577 A1 | 1/2004 | Emerson Campbell et al. |
| 2004/0029177 A1 | 2/2004 | Nadaoka et al. |
| 2004/0175756 A1 | 9/2004 | Kolkman et al. |
| 2005/0048512 A1 | 3/2005 | Kolkman et al. |
| 2005/0053973 A1 | 3/2005 | Kolkman et al. |
| 2005/0054078 A1 | 3/2005 | Miller et al. |
| 2005/0089932 A1 | 4/2005 | Koklman et al. |
| 2005/0221384 A1 | 10/2005 | Kolkman et al. |
| 2006/0115866 A1 | 6/2006 | Ohashi |
| 2006/0160164 A1 | 7/2006 | Miller et al. |
| 2006/0263836 A1 | 11/2006 | Connelley et al. |
| 2007/0287197 A1 | 12/2007 | Harris et al. |
| 2009/0005267 A1 * | 1/2009 | Love ................... G01N 33/743 506/18 |
| 2009/0253219 A1 * | 10/2009 | Bauer .............. G01N 33/54386 436/514 |
| 2009/0269777 A1 | 10/2009 | Birkenmeyer et al. |
| 2010/0105874 A1 | 4/2010 | Schuurman et al. |
| 2010/0167301 A1 | 7/2010 | Collier et al. |
| 2011/0117674 A1 | 5/2011 | Melin et al. |
| 2012/0308997 A1 | 12/2012 | Ruan et al. |
| 2014/0273035 A1 | 9/2014 | Dowell et al. |
| 2014/0273272 A1 | 9/2014 | Gayda et al. |

(Continued)

FOREIGN PATENT DOCUMENTS

| CN | 101278194 A | 10/2008 |
|---|---|---|
| CN | 101946179 A | 1/2011 |
| CN | 102066936 A | 5/2011 |

(Continued)

OTHER PUBLICATIONS

CN patent application No. 2016052601699800, Office Action dated May 31, 2016.
JP patent application No. 2016-500133, Office Action dated Sep. 6, 2016.
PCT Invitation to Pay Additional Fees and, Where Applicable, Protest Fee dated Mar. 14, 2014 issued in PCT/US2013/077063.
PCT International Search Report and Written Opinion dated Jun. 4, 2014 issued in PCT/US2013/077063.
PCT International Search Report and Written Opinion dated Mar. 6, 2014 issued in PCT/US2013/077073.
PCT International Preliminary Report on Patentability dated Sep. 15, 2015 issued in PCT/US2013/077063.

(Continued)

*Primary Examiner* — Changhwa J Cheu

(74) *Attorney, Agent, or Firm* — Jennifer L. Wahlsten; Weaver Austin Villeneuve & Sampson; Audrey L. Bartnicki

(57) ABSTRACT

Provided herein are assays and kits useful for avoiding "prozone phenomenon" or "hook effect" and which expand the range of accurately measurable analyte concentrations.

11 Claims, 10 Drawing Sheets

(56) References Cited

U.S. PATENT DOCUMENTS

2014/0322724 A1 10/2014 Walshe

FOREIGN PATENT DOCUMENTS

| | | |
|---|---|---|
| EP | 0 916 951 B1 | 1/2003 |
| EP | 1 361 435 A1 | 11/2003 |
| EP | 2 405 019 A1 | 1/2012 |
| JP | S60-501776 A | 10/1985 |
| JP | H03-504276 | 9/1991 |
| WO | 85/02258 | 5/1985 |
| WO | WO 89/11101 | 11/1989 |
| WO | WO 91/19196 | 12/1991 |
| WO | WO 95/17675 | 6/1995 |
| WO | WO 98/39657 | 9/1998 |
| WO | WO 99/51773 | 10/1999 |
| WO | WO 00/56934 | 9/2000 |
| WO | WO 2007/089564 | 8/2007 |
| WO | WO 2008/020823 | 2/2008 |
| WO | WO 2009/078875 | 6/2009 |
| WO | WO 2009/126336 | 10/2009 |
| WO | WO 2009/128774 | 10/2009 |
| WO | WO 2011/097552 | 8/2011 |
| WO | WO 2012/142242 | 10/2012 |
| WO | WO 2012/170428 | 12/2012 |
| WO | WO 2013/088429 | 6/2013 |
| WO | WO 2014/143323 | 9/2014 |
| WO | WO 2014/149111 | 9/2014 |

OTHER PUBLICATIONS

PCT International Preliminary Report on Patentability dated Sep. 15, 2015 issued in PCT/US2013/077073.

Adamczyk, et al. (2003) "Regiodependent Luminescence Quenching of Biotinylated N-Sulfonyl-acridinium-9-carboxamides by Avidin," *Organic Letters* 5(21): 3779-3782.

Adamczyk, et al. (2004) "Chemiluminescence Quenching of Pteroic Acid-N-sulfonyl-acridinium-9-carboxamide Conjugates by Folate Binding Protein," *Bioorganic and Medicinal Chemistry Letters* 14: 2313-2317.

Adamczyk, et al. (2004) "Intrinsic Factor-Mediated Modulation of Cyanocobalamin-N-sulfonylacridinium-9-carboxamide Chemiluminescence," *Bioorganic and Medicinal Chemistry Letters* 14: 3917-3921.

Adamczyk, et al. (2006)"Chemiluminescent Acridinium-9-Carboxamide Boronic Acid Probes: Application to a Homogeneous Glycated Hemoglobin Assay," *Bioorganic & Medicinal Chemistry Letters* 16: 1324-1328.

Beste, et al. (1999) "Small Antibody-Like Proteins with Prescribed Ligand Specificities Derived from the Lipocalin Fold," *Proceedings of the National Academy of Sciences* 96(5): 1898-1903.

Fernando, et al. (1992) "Studies of the 'hook' effect in the one-step sandwich homogeneous immunoassay" *Journal of Immunological Methods* 151(1-2):47-66.

Fernando, et al. (1992) "Studies of the low dose 'hook' effect in a competitive homogeneous immunoassay," *Journal of Immunological Methods* 151(1-2):27-46.

Frengen, et al. (1995) "A sequential binding assay with a working range extending beyond seven orders of magnitude," *Journal of Immunological Methods* 178(1):131-40.

Kartalov, et al. (2008) "Internally calibrated quantification of protein analytes in human serum by fluorescence immunoassays in disposable elastomeric microfluidic devices," *Electrophoresis* 29(24):5010-5016.

Ku et al. (1995) "Alternate Protein Frameworks for Molecular Recognition" *Proc. Natl. Acad. Sci. USA* 92: 6552-6556.

Lindmo, et al. (1990) "Immunometric assay by flow cytometry using mixtures of two particle types of different affinity," *Journal of Immunological Methods* 126(2):183-189.

Murali et al. (2003) "Antibody Like Peptidomimetics as Large Scale immunodetection Probes" *Cell. Mol. Bioi.* 49(2): 209-216 Medline Abstract only.

Ohmura, et al. (2003) "Combinational use of antibody affinities in an immunoassay for extension of dynamic range and detection of multiple analytes," *Analytical Chemistry* 75(1):104-110.

Olejniczak, et al. (2010) "Rapid Determination of Antigenic Epitopes in Human NGAL Using NMR" *Biopolymers* 93(7): 657-667.

Polak (1977) "Introduction to Immunocytochemistry," 2nd Edition, pp. 5-10.

Polak, et al., "Introduction to Immunocytochemistry", 2nd Edition, Springer-Verlag, 1997, Table of Contents.

Silverman et al. (2005) "Multivalent Avimer Proteins Evolved by Exon Shuffling of a Family of Human Receptor Domains" *Nature Biotechnology* 23(12):1556-1561.

Chinese Supplementary Search Report dated Feb. 28, 2017 issued in CN 201380075980.5.

Japanese Second Office Action dated May 30, 2017 issued in JP 2016-500133.

* cited by examiner

ASSAY WITH INCREASED DYNAMIC RANGE

CROSS-REFERENCE TO RELATED APPLICATIONS

This application is a divisional of U.S. application Ser. No. 13/833,655, filed on Mar. 15, 2013, which is hereby incorporated herein by reference in its entirety for all purposes.

FIELD

Provided herein are kits and methods for expanding the dynamic range of an assay.

BACKGROUND

For the past several decades, assays have been performed using fluorescence, chemiluminescence, or other means of generating a signal in response to an analyte. Currently, many assays are performed by measurement of the intensity of a light signal generated in the total volume of a reaction mixture. The light signal generated can be measured by an optical means, wherein the light signal generated is emitted by a large number of molecules. In a typical embodiment, these assays can be carried out by combining a sample suspected of containing an antigen with a reagent comprising a first antibody attached to a solid support, e.g., a microparticle, to form a reaction mixture. The antigen, if present in the sample, specifically binds to the first antibody. A conjugate, which comprises a second antibody having a label attached thereto, is introduced to the reaction mixture and specifically binds to the antigen, which is specifically bound to the first antibody, which, as stated previously, is attached to the solid support. Such an assay is referred to as a sandwich assay or an immunometric assay. This type of assay is shown schematically in FIG. 1. The signal attributable to the label is then measured after unbound conjugate is removed from the reaction mixture, typically by performing a wash step. The signal that is derived from the total volume of the reaction mixture is measured and then compared to a calibration curve to establish the concentration of antigen present in the sample. When the assay includes a washing step to remove unbound sample analyte before introducing the conjugate antibody, it generally is considered as a "two-step assay". When the assay introduces the conjugate antibody and the analyte to antibody coated microparticles together without intermediate washing steps, it is considered as "one-step" assay. "Hook effect" or "Prozone phenomenon" is a phenomenon of falsely low values on an assay when an overwhelming amount of antigen is present in a "one-step assay" format. It is caused by insufficient capture antibody and detection antibody in an assay. Such hook effect limits assay dynamic range.

A sandwich assay can detect a wide range of analyte concentrations; typically it can accurately measure analyte concentration by 2-3 orders of magnitude. But it is uncommon to extend analyte detection more broadly, e.g., over 3 orders of magnitude.

SUMMARY

In one aspect, provided are kits. In varying embodiments, the kits comprise:
 i) a first analyte-binding molecule comprising a first label;
 ii) a second analyte-binding molecule comprising a second label, wherein the binding affinity for the analyte of the first analyte-binding molecule is greater than that of the second analyte-binding molecule, and
 iii) a third analyte-binding molecule attached to a solid support, wherein the third analyte-binding molecule can bind to analyte concurrently with either the first analyte-binding molecule or the second analyte-binding molecule. In some embodiments, the first analyte-binding molecule and the second analyte-binding molecule are directly attached to the label. In some embodiments, one or more of the first analyte-binding molecule, the second analyte-binding molecule, and/or the third analyte-binding molecule is an antibody or fragment thereof. In some embodiments, the solid support is selected from the group consisting of a particle, a microparticle, a bead, an electrode, and a multiwell plate. In some embodiments, the solid support comprises two or more spatially separated electrodes. In some embodiments, the solid support comprises a microparticle. In some embodiments, one or both of the first label and the second label are selected from the group consisting of an enzyme, a chromophore, and a fluorophore. In some embodiments, the first label and the second label are different. In some embodiments, the difference in binding affinity of the first analyte-binding molecule and the second analyte-binding molecule for the analyte ranges from about 5-fold to about 100-fold, e.g., from about 10-fold to about 100-fold. In some embodiments, the difference in binding affinity of the first analyte-binding molecule and the second analyte-binding molecule for the analyte is at least about 100-fold. In some embodiments, the kits can be employed for either a one-step or two-step sandwich assay.

In some embodiments, the kits comprise:
 i) a first analyte-binding molecule attached to a first solid support;
 ii) a second analyte-binding molecule attached to a second solid support, wherein the binding affinity for the analyte of the first analyte-binding molecule is greater than that of the second analyte-binding molecule; and
 iii) a third analyte-binding molecule comprising a label, wherein the third analyte-binding molecule can bind to analyte concurrently with either the first analyte-binding molecule or the second analyte-binding molecule. In some embodiments, one or more of the first analyte-binding molecule, the second analyte-binding molecule, and/or the third analyte-binding molecule is an antibody or fragment thereof. In some embodiments, the third analyte-binding molecule is directly attached to the label. In some embodiments, the label is selected from the group consisting of an enzyme, a chromophore, and a fluorophore. In some embodiments, the first solid support and the second solid support are independently selected from the group consisting of a particle, a microparticle, a bead, an electrode and a multiwell plate. In some embodiments, the first solid support is a microparticle or bead comprising a first chromophore and the second solid support is a microparticle or bead comprising a second chromophore. In some embodiments, the first solid support and the second solid support are microparticles which differ in either shape or size. In some embodiments, the first solid support is a first electrode and the second solid support is a second electrode, wherein the first electrode and the second electrode are spatially separated. In some embodiments, the difference in binding affinity of the first analyte-binding molecule and the second analyte-binding molecule for the analyte ranges from about 5-fold to about 100-fold, e.g., from about 10-fold to about 100-fold. In some embodiments, the difference in binding affinity of the first analyte-binding molecule and the second analyte-binding molecule for the analyte is at least about 100-fold.

In some embodiments, e.g., as for a competitive assay kit, the kits comprise:

i) a first analyte-binding molecule attached to a first solid support;

ii) a second analyte-binding molecule attached to a second solid support, wherein the binding affinity for the analyte of the first analyte-binding molecule is greater than that of the second analyte-binding molecule; and iii) a tracer comprising said analyte or fragment thereof attached to a label, wherein said tracer can compete with said analyte for binding to either the first analyte-binding molecule or the second analyte-binding molecule. In some embodiments, the kits comprise one or more of the first analyte-binding molecule, and/or the second analyte-binding molecule, is an antibody or fragment thereof. In some embodiments, the label is selected from the group consisting of an enzyme, a chromophore, and a fluorophore. In some embodiments, the first solid support and the second solid support are independently selected from the group consisting of a particle, a microparticle, a bead, an electrode and a multiwell plate. In some embodiments, the first solid support is a microparticle or bead comprising a first chromophore and the second solid support is a microparticle or bead comprising a second chromophore. In some embodiments, the first solid support and the second solid support are microparticles which differ in either shape or size. In some embodiments, the first solid support is a first electrode and the second solid support is a second electrode, wherein the first electrode and the second electrode are spatially separated. In some embodiments, the difference in binding affinity of the first analyte-binding molecule and the second analyte-binding molecule for the analyte ranges from about 5-fold to about 100-fold, e.g., from about 10-fold to about 100-fold. In some embodiments, the difference in binding affinity of the first analyte-binding molecule and the second analyte-binding molecule for the analyte is at least about 100-fold.

In another aspect, provided are methods of expanding the dynamic range of an assay. In varying embodiments, the methods comprise:

a) contacting a test sample suspected of comprising an analyte with a first analyte-binding molecule comprising a first label, a second analyte-binding molecule comprising a second label and a third analyte-binding molecule attached to a solid support under conditions that allow binding of:

(i) the first analyte-binding molecule and the third analyte-binding molecule and (ii) the second analyte-binding molecule and the third analyte-binding molecule to the analyte, wherein the binding affinity for the analyte of the first analyte-binding molecule is greater than that of the second analyte-binding molecule, wherein the first analyte-binding molecule and the second analyte-binding molecule do not concurrently bind to the analyte;

b) measuring the signal intensities of the first label of the first analyte-binding molecule bound to the analyte and of the second label of the second analyte-binding molecule bound to the analyte; and c) determining the concentration of analyte by comparing the signal intensities of the first label and the second label. In some embodiments, one or more of the first analyte-binding molecule, the second analyte-binding molecule, and/or the third analyte-binding molecule is an antibody or fragment thereof. In some embodiments, the first analyte-binding molecule and the second analyte-binding molecule are directly attached to the label. In some embodiments, the solid support is selected from the group consisting of a particle, a microparticle, a bead, an electrode and a multiwell plate. In some embodiments, one or both of the first label and the second label are selected from the group consisting of an enzyme, a chromophore, and a fluorophore. In some embodiments, the first analyte-binding molecule and the second analyte-binding molecule are contacted with the test sample in the same reaction mixture. In some embodiments, the first analyte-binding molecule and the second analyte-binding molecule are contacted with the test sample in the different reaction mixtures. In some embodiments, the first label and the second label are different. In some embodiments, the difference in binding affinity of the first analyte-binding molecule and the second analyte-binding molecule for the analyte ranges from about 5-fold to about 100-fold. In some embodiments, the difference in binding affinity of the first analyte-binding molecule and the second analyte-binding molecule for the analyte is at least about 100-fold. In varying embodiments, the dynamic range of the assay comprises three or more orders of magnitude, e.g., four or more orders of magnitude. In some embodiments, the first analyte-binding molecule and the second analyte-binding molecule are present in predetermined molar amounts that differ by less than about 100-fold (e.g., from about 10-fold to about 100-fold, from about 10-fold to about 50-fold, from about 60-fold to about 100-fold, about 25-fold, about 50-fold, about 75-fold). In some embodiments, the first analyte-binding molecule and the second analyte-binding molecule are not oligomerized or cross-linked. In some embodiments, the method is performed using an automated or semi-automated system. In some embodiments, the assay is a one-step assay.

In some embodiments, step b) of measuring the signal intensities of the first label of the first analyte-binding molecule bound to the analyte and the signal intensity of the second label of the second analyte-binding molecule bound to the analyte is done in a calibration assay over a predetermined range of analyte concentrations, and the method further comprises the step of:

d) establishing a flag value by determining a ratio of the signal intensity of the first label of the first analyte-binding molecule bound to the analyte and the signal intensity of the second label of the second analyte-binding molecule bound to the analyte in the calibration assay or the inverse of this ratio at or near the concentration of analyte that provides maximum signal intensity of the first label of the first analyte-binding molecule bound to the analyte.

In some embodiments, when the ratio of the signal intensity of the second label of the second analyte-binding molecule bound to the analyte to the signal intensity of the first label of the first analyte-binding molecule bound to the analyte in the test sample:

exceeds or equals the flag value, then the sinking section of the calibration curve from the signal intensity of the first label of the first analyte-binding molecule bound to the analyte is used to determine analyte concentration; or is less than the flag value, then the rising section of the calibration curve from the signal intensity of the first label of the first analyte-binding molecule bound to the analyte is used to determine analyte concentration.

In some embodiments, when the ratio of the signal intensity of the first label of the first analyte-binding molecule bound to the analyte to the signal intensity of the second label of the second analyte-binding molecule bound to the analyte in the test sample:

is less than or equals the flag value, then the sinking section of the calibration curve from the signal intensity of the first label of the first analyte-binding molecule bound to the analyte is used to determine analyte concentration; or exceeds the flag value, then the rising section of the calibration curve from the signal intensity of the first label of the first analyte-binding molecule bound to the analyte is used to determine analyte concentration.

In a further aspect, provided are methods of expanding the dynamic range of an assay. In some embodiments, the methods comprise:

a) contacting a test sample suspected of comprising an analyte with a first analyte-binding molecule attached to a first solid support, a second analyte-binding molecule attached to a second solid support, and a third analyte-binding molecule comprising a label under conditions that allow binding of:

(i) the third analyte-binding molecule to the first solid support via the analyte bound to the first analyte-binding molecule; and (ii) the third analyte-binding molecule to the second solid support via the analyte bound to the second analyte-binding molecule; and wherein the binding affinity for the analyte of the first analyte-binding molecule is greater than that of the second analyte-binding molecule, wherein the first analyte-binding molecule and the second analyte-binding molecule do not concurrently bind to the analyte;

b) measuring the signal intensities from the label of the third analyte-binding molecule bound to the first solid support and to the second solid support; and c) determining the concentration of analyte by comparing the signal intensities from the label of the third analyte-binding molecule bound to the first solid support and to the second solid support. In some embodiments, one or more of the first analyte-binding molecule, the second analyte-binding molecule, and/or the third analyte-binding molecule is an antibody or fragment thereof. In some embodiments, the third analyte-binding molecule is directly attached to the label. In some embodiments, the first solid support and the second solid support are independently selected from the group consisting of a particle, a microparticle, a bead, an electrode and a multiwell plate. In some embodiments, one or both of the first label and the second label are selected from the group consisting of an enzyme, a chromophore, and a fluorophore. In some embodiments, the first analyte-binding molecule and the second analyte-binding molecule are contacted with the test sample in the same reaction mixture. In some embodiments, the first solid support is a microparticle or bead comprising a first chromophore and the second solid support is a microparticle or bead comprising a second chromophore. In some embodiments, the first solid support and the second solid support are microparticles which differ in either shape or size. In some embodiments, the first solid support is a first electrode and the second solid support is a second electrode, wherein the first electrode and the second electrode are spatially separated. In some embodiments, the first electrode and the second electrode are contained in a handheld point-of-care device. In some embodiments, the first analyte-binding molecule and the second analyte-binding molecule are contacted with the test sample in the different reaction mixtures. In some embodiments, the difference in binding affinity of the first analyte-binding molecule and the second analyte-binding molecule for the analyte ranges from about 5-fold to about 100-fold, e.g., from about 10-fold to about 100-fold. In some embodiments, the difference in binding affinity of the first analyte-binding molecule and the second analyte-binding molecule for the analyte is at least about 100-fold. In some embodiments, the dynamic range of the immunoassay comprises three or more orders of magnitude. In some embodiments, the first analyte-binding molecule and the second analyte-binding molecule are present in predetermined molar amounts that differ by less than about 100-fold (e.g., from about 10-fold to about 100-fold, from about 10-fold to about 50-fold, from about 60-fold to about 100-fold, about 25-fold, about 50-fold, about 75-fold). In some embodiments, the first analyte-binding molecule and the second analyte-binding molecule are not oligomerized or cross-linked. In some embodiments, the method is performed using an automated or semi-automated system.

In some embodiments, the foregoing assay is a one-step assay (i.e., where there is no wash step). In some embodiments, the foregoing assay is a two-step assay (i.e., where there is a wash step). Such a two-step assay can be carried out as described, except that optionally, analyte that is not bound to said first or said second solid support is removing by washing before contacting the test sample, the first analyte-binding molecule attached to the first solid support, and the second analyte-binding molecule attached to the second solid support, with the third analyte-binding molecule comprising a label. Washing can be done by means that are well known to those skilled in the art.

In some embodiments of the one-step assay, step b) of measuring the signal intensities of the label bound to analyte and the first analyte-binding molecule attached to first solid support and the signal intensity of the label bound to analyte and second analyte-binding molecule attached to second solid support is done in a calibration assay over a predetermined range of analyte concentrations, and the method further comprises the step of:

d) establishing a flag value by determining a ratio of the signal intensity of the label bound to analyte and first analyte-binding molecule attached to first solid support and the signal intensity of the label bound to analyte and second analyte-binding molecule attached to second solid support in the calibration assay or the inverse of this ratio at or near the concentration of analyte that provides maximum signal intensity of the label bound to analyte and first analyte-binding molecule attached to first solid support.

In some embodiments of the one-step assay, when the ratio of the signal intensity of the second label of the second analyte-binding molecule bound to the analyte to the signal intensity of the first label of the first analyte-binding molecule bound to the analyte in the test sample:

exceeds or equals the flag value, the sinking section of the calibration curve from the signal intensity of the first label of the first analyte-binding molecule bound to the analyte is used to determine analyte concentration, or is less than the flag value, the rising section of the calibration curve from the signal intensity of the first label of the first analyte-binding molecule bound to the analyte is used to determine analyte concentration.

In some embodiments of the one-step assay, when the ratio of the signal intensity of the first label of the first analyte-binding molecule bound to the analyte to the signal intensity of the second label of the second analyte-binding molecule bound to the analyte in the test sample:

is less than or equals the flag value, the sinking section of the calibration curve from the signal intensity of the first label of the first analyte-binding molecule bound to the analyte is used to determine analyte concentration; or exceeds the flag value, the rising section of the calibration curve from the signal intensity of the first label of the first analyte-binding molecule bound to the analyte is used to determine analyte concentration.

In some embodiments of the two-step assay, the method comprises a further step b) of measuring the signal intensities of the label bound to analyte and first analyte-binding molecule attached to first solid support and the signal intensity of the label bound to analyte and second analyte-binding molecule attached to second solid support is done in a calibration assay over a predetermined range of analyte concentrations. The method further optionally comprises the step of establishing criteria to select adequate sections of the two signal plots to be used as the calibration curve. In some embodiments, the method further comprises the step of establishing a flag value at or near the leveling off value (plateau) of the signal intensity of the label bound to analyte and first analyte-binding molecule attached to first solid support. In some embodiment of the method, when the signal intensity of the label bound to analyte and first analyte-binding molecule attached to first solid support is equal to or higher than the flag value, then the rising section of the calibration curve from the signal intensity of the label bound to analyte and second analyte-binding molecule attached to second solid support is used to determine analyte concentration.

In a further aspect, provided are methods of expanding the dynamic range of an assay in competitive assay format. In some embodiments, the methods optionally comprise:

a) contacting a test sample suspected of comprising an analyte with tracer comprising said analyte or fragment thereof attached to a label, a first analyte-binding molecule attached to a first solid support, a second analyte-binding molecule attached to a second solid support, wherein the binding affinity for the analyte of the first analyte-binding molecule is greater than that of the second analyte-binding molecule, wherein the first analyte-binding molecule and the second analyte-binding molecule do not concurrently bind to the analyte;

b) measuring the signal intensities from the tracer bound to the first analyte-binding molecule on the first solid support and the second analyte-binding molecule on the second solid support; and c) establishing a flag value at or near the leveling off value (plateau) of the signal intensity of the tracer bound to the first analyte-binding protein attached to the first solid support. In some embodiments, when the signal intensity of the tracer bound to the first analyte-binding protein attached to the first solid support is equal to or less than the flag value, then the sinking section of the calibration curve from the signal intensity of the tracer bound to the second analyte-binding molecule attached to the second solid support is used to determine analyte concentration.

BRIEF DESCRIPTION OF THE DRAWINGS

FIG. 6A shows an illustrative signal plot obtained independently from exemplary high affinity and low affinity antibodies. Each plot has a rising section and a sinking section of the calibration curve, and a maximum intensity peak. FIG. 6B shows the signal ratio plot from low affinity antibody and high affinity antibody. These two plots can be used in combination to determine the concentration of a test sample.

FIG. 7A shows an illustrative signal plot obtained independently from the high affinity and low affinity antibodies. FIG. 7B shows the signal ratio plot from low affinity antibody and high affinity antibody. These two plots can be used in combination to determine the concentration of a test sample.

FIG. 8A shows an illustrative signal plot obtained independently from the high affinity and low affinity antibodies. FIG. 8B shows the signal ratio plot from low affinity antibody and high affinity antibody. These two plots can be used in combination to determine the concentration of a test sample.

DETAILED DESCRIPTION

The present disclosure is predicated, in part, on the discovery and design of assays and methods for increasing assay dynamic range by eliminating or avoiding so-called "hook effect" or "prozone phenomenon" in, e.g., sandwich assays, including one-step and two-step sandwich assays.

Definitions

The following terms are relevant to the present disclosure:

The terms "hook effect" and "prozone phenomenon" interchangeably refer to measured levels of analyte (e.g., antigen) displaying a significantly lower absorbance than the actual level present in a sample. This can be caused by a number of factors. For instance, it occurs when an assay is saturated by concentrations of analyte sufficiently high to supersaturate all available sites on both the capture analyte-binding molecule as well as the detection analyte-binding molecule, thereby preventing the sandwich-formation. The analyte-saturated detection binding molecules in solution remain unbound and are washed off giving a falsely low signal. A "hook" is observed in the curve when data is plotted as a signal versus analyte (e.g., antigen) concentration.

Figure 3:
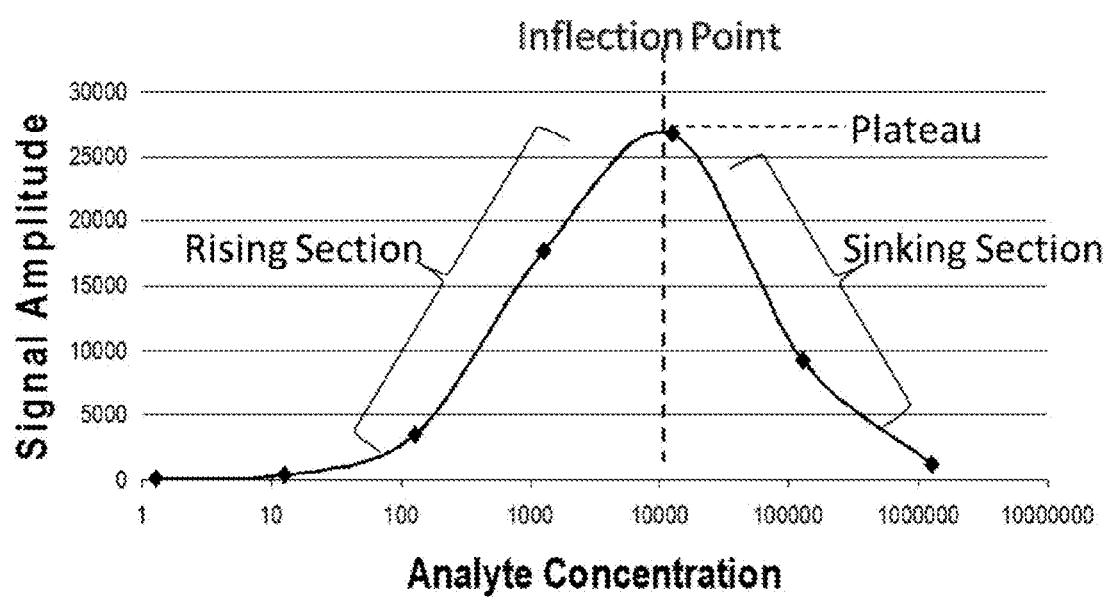
FIG. 3 shows a representative calibration curve generated as a result of a hook effect with lack of a hook effect illustrated by the line marked "plateau". Abscissa: Analyte Concentration (e.g., units such as ng/mL). Ordinate: Signal Amplitude (e.g., units such as Relative Light Unit counts).

For example, in a typical two antibody single-step "sandwich-type" immunoassay, a capture antibody (which is an antibody that is typically immobilized onto a solid phase) is mixed with a test sample suspected of containing an analyte of interest. To this mixture an antibody containing a detectable label (hereinafter referred to as a "conjugate") is added. In this assay, the capture antibody binds to the analyte in the test sample to form a capture antibody-analyte complex. The conjugate then binds to the capture antibody-analyte complex (the "sandwich") and the conjugate label is detected as a measure of the analyte of interest using routine techniques known in the art. In the presence of a large excess of free analyte, all of the conjugate binds directly to the free analyte, resulting in less conjugate being available to bind to the capture antibody-analyte complex. Consequently, because less free conjugate is available to bind to the capture antibody-analyte complex, the amount of label bound to the capture antibody-analyte complex is reduced, thus reducing the amount of analyte detected. FIG. 3 shows an example of the calibration curve generated as a result of hook effect. As evidenced by FIG. 3, paradoxically, at the high end range of analyte concentration, the higher the actual analyte concentration is the lower its measured concentration will appear. This is in contrast to a curve obtained where there is no hook effect. Such a calibration curve does not decrease to lower values, but instead remains in the plateau.

The calibration curve with hook effect thus will have a peak and two characteristic sections, a "rising section" and a "sinking section". As can be seen from FIG. 3, the rising section is the section of the calibration curve that is increasing to higher values. The sinking section is the section of the calibration curve that is decreasing to lower or even negative values. The rising section is concave upwards (positive curvature) whereas the sinking section is concave downwards (negative curvature). The rising section and sinking section are separated by an inflection point where the concavity changes from minus to plus. The hook effect and same type of calibration curve can be observed in a one-step sandwich assay.

An "assay" is a biochemical test that measures the presence or concentration of a substance in solutions that frequently contain a complex mixture of substances. Analytes in biological liquids such as serum or urine are frequently assayed using assay methods. Such assays are based on the unique ability of an analyte-binding molecule (e.g., antibody or antigenically reactive fragment thereof) to bind with high specificity to one or a very limited group of molecules. A molecule that binds to an analyte-binding molecule (e.g., antibody or antigenically reactive fragment thereof) is called an analyte or antigen. Assays requiring a separation step, often called separation assays or heterogeneous assays, are popular because they are easy to design, but they frequently require multiple steps including careful washing of a surface onto which the labeled reagent has bound. Some assays can be run without a separation step. Such assays can frequently be carried out simply by mixing the reagents and sample and making a physical measurement. Such assays are called homogeneous assays, or, less frequently, non-separation assays.

Figure 1:
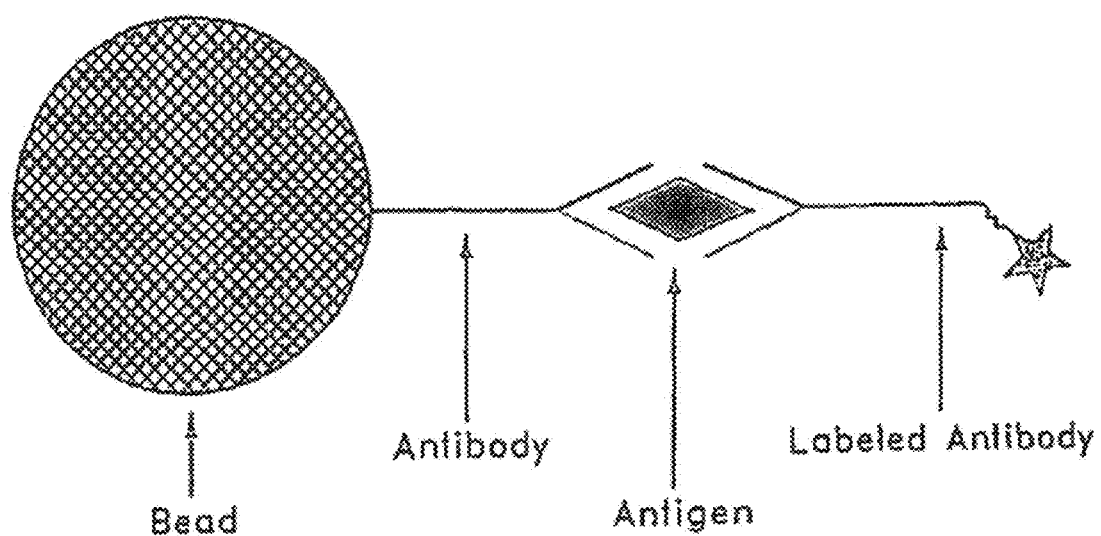
FIG. 1 provides an illustrative schematic of a sandwich assay.

As used herein, the expression "sandwich assay" means an assay that employs two analyte-binding molecules that concurrently (e.g., in the same or separate steps) bind to the same analyte. One of the analyte-binding molecules is attached, directly or indirectly, to a solid support, allowing the analyte to be attached directly or indirectly to the solid support, such as, for example, a microparticle or an electrode. The other analyte-binding molecule is attached, directly or indirectly, to a label, allowing the analyte to be attached directly or indirectly to the label to provide a signal for detecting the analyte. For example, one of the analyte-binding molecules can be a capture analyte-binding molecule (e.g., antibody or antigenically reactive fragment thereof) for specifically binding to an analyte (e.g., antigen) in a sample, whereby the analyte (e.g., antigen) is attached directly or indirectly to a solid support, such as, for example, an electrode or a microparticle, and the other analyte-binding molecule can be a detection analyte-binding molecule (e.g., antibody or antigenically reactive fragment thereof) for specifically binding to the analyte (e.g., antigen) in the sample, whereby the analyte (e.g., antigen) is attached directly or indirectly to a label for detecting the antigen. If a relatively high amount of analyte is present in the sample, a higher signal will be produced. If a relatively low amount of analyte is present in the sample, a lower signal will be produced. FIG. 1 is a schematic diagram illustrating a representative example of a sandwich assay.

Figure 2:
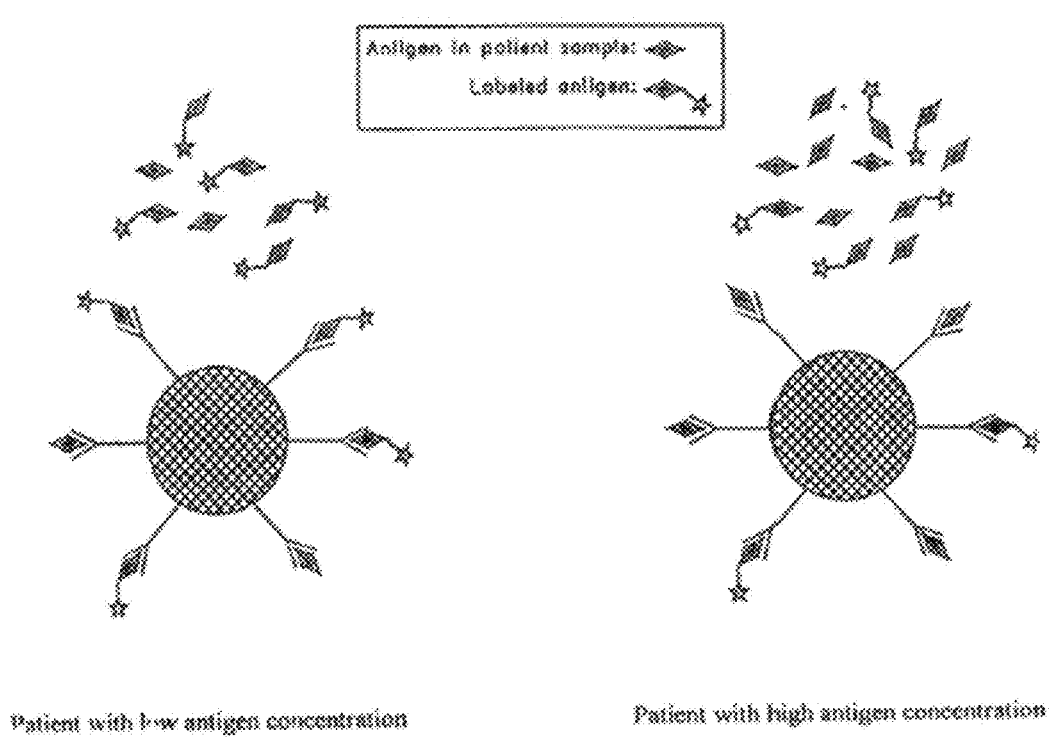
FIG. 2 provides an illustrative schematic of a competitive assay.

As used herein, the expression "competitive assay" refers to an assay in which an unlabeled antigen and a labeled antigen compete for binding to the same antibody site. Alternatively, an antibody and a labeled antibody compete for binding to the same antigen site. In an example of the former, a labeled antigen and an unlabeled antigen are used. A solid support is coated with an antibody that can specifically bind to either the labeled antigen or to the unlabeled antigen. The solid support, the labeled antigen, and a patient's sample suspected of containing the antigen are combined. Of course, any antigen in the patient's sample is unlabeled. The labeled antigen and the unlabeled antigen compete for antibody sites on the solid support. Only when the labeled antigen attaches to the antibody on the solid support can a signal be produced, because only the labeled antigen can generate a signal. The amount of antigen in the patient's sample is inversely proportional to the amount of signal produced. This type of assay is shown schematically in FIG. 2.

As used herein, the term "complex" means at least two molecules that are specifically bound to one another. Examples of complexes include, but are not limited to, an analyte bound to an analyte-binding molecule, an analyte bound to a plurality of analyte-binding molecules, e.g., an analyte bound to two analyte-binding molecules, an analyte-binding molecule bound to a plurality of analytes, e.g., an analyte-binding molecule bound to two analytes.

As used herein, the expression "solid support" means any solid surface to which an analyte-binding molecule (e.g., antibody or antigenically reactive fragment thereof) can be attached such that the analyte-binding molecule cannot break free from the solid support in a liquid medium. A solid support can easily be separated from a liquid which the solid support contacts. In varying embodiments, the solid support can be, for example, plastic, derivatized plastic, magnetic or non-magnetic metal, glass or silicon. Representative examples of solid supports, include without limitation, electrodes, test tubes, beads, microparticles, nanoparticles, wells of micro- or multi-well plates, gels, colloids, biological cells, sheet, chip, and other configurations known to those of ordinary skill in the art. An example of an item to which an analyte-binding molecule (e.g., antibody or antigenically reactive fragment thereof) can be attached is a microparticle, such as, for example, a magnetic microparticle. Microparticles typically have an average diameter of less than 1000 microns. The microparticle can easily be separated from a liquid in which it is dispersed. The microparticle is readily dispersed in an aqueous medium. Moreover, optionally the solid support provides a means of recovery of the analyte-binding protein—i.e., means of release or detachment of the analyte-binding molecule from the surface under controlled conditions distinct from those in which the assay is conducted. For example, the analyte-binding molecule may be attached to the solid support by means of a cleavable linker.

As used herein, the expression "capture analyte-binding molecule" means an analyte-binding molecule (e.g., antibody or antigenically reactive fragment thereof) that binds an analyte, e.g., an antigen, to a solid support, with the result that the antibody attaches the analyte to the solid support, whereby the analyte is attached to the solid support either directly or indirectly through an intervening moiety.

As used herein the expression "detection analyte-binding molecule" means an analyte-binding molecule (e.g., antibody or antigenically reactive fragment thereof) that is attached to a moiety that provides or can be made to provide a detectable signal in a chemical or biological reaction.

The term "one-step" assay refers to an assay that does not includes a separation of bound from unbound sample analyte.

The term "two-step" assay refers to an assay that includes a separation of bound from unbound sample analyte.

"About" refers to approximately a +/−10% variation from the stated value. It is to be understood that such a variation is always included in any given value provided herein, whether or not specific reference is made to it.

"Analyte," as further described herein, means a compound or composition to be measured, which may be a ligand, which is monoepitopic or polyepitopic, antigenic or haptenic, a single or plurality of compounds which share at least one common epitopic site or a receptor. Illustrative analytes of interest include without limitation, e.g., proteins, glycoproteins, peptides, polypeptides, oligonucleotides or polynucleotides generally, as well as more specifically, e.g., antibodies, antigens, haptens, hormones, drugs, enzymes, or receptors.

"Antibody" and "antibodies" refer to monoclonal antibodies, multispecific antibodies, bifunctional antibodies, human antibodies, humanized antibodies (fully or partially humanized), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11): 1290-1297 (2007), and International Patent Application Publication No. WO 2001/058956, the contents of each of which are herein incorporated by reference), and functionally active epitope-binding fragments of any of the above. The term "bifunctional antibody," as used herein, refers to an antibody that comprises a first arm having a specificity for one antigenic site and a second arm having a specificity for a different antigenic site, i.e., the bifunctional antibodies have a dual specificity.

"Antibody fragment" and "antibody fragments" refer to a portion of an intact antibody comprising the antigen-binding site or variable region. The portion does not include the constant heavy chain domains (i.e., CH2, CH3 or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Binding Constants" are as described herein. The term "association rate constant," "$k_{on}$" or "$k_a$" as used interchangeably herein, refers to the value indicating the binding rate of a first member of a specific binding pair (SBP1; e.g., an analyte-binding molecule, an antibody (Ab) or analyte reactive fragment thereof) and a second member of a specific binding pair (SBP2; e.g., an analyte (e.g., antigen (Ag)) or the rate of complex formation between the first member of the specific binding pair and the second member of the specific binding pair as shown by the equations below:

$$SBP1 + SBP2 \rightarrow SBP1-SBP2$$

$$Ab + Ag \rightarrow Ab-Ag.$$

The term "dissociation rate constant," "$k_{off}$" or "$k_d$" as used interchangeably herein, refers to the value indicating the dissociation rate of SBP1 (e.g., an analyte-binding molecule, an Ab or analyte-reactive fragment thereof) from SBP2 (e.g., Ag) or separation of SBP1-SBP2 complex (e.g., Ab-Ag complex) over time into free SBP1 (e.g., an analyte-binding molecule, an Ab or analyte-reactive fragment thereof) and SBP2 (e.g., Ag) as shown by the equation below:

$$SBP1 + SBP2 \leftarrow SBP1-SBP2$$

$$Ab + Ag \leftarrow Ab-Ag.$$

Methods for determining association and dissociation rate constants are well-known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) also can be used.

The term "equilibrium dissociation constant" or "KD" as used interchangeably herein, refers to the value obtained by dividing the dissociation rate ($k_{off}$) by the association rate ($k_{on}$). The association rate, the dissociation rate and the equilibrium dissociation constant are used to represent the binding affinity of an analyte-binding molecule (e.g., antibody or analyte-reactive fragment thereof) to an antigen. This can be described by the following reaction and equation:

$$A+B \rightarrow AB$$

$$K_D = \frac{[AB]}{[A][B]}.$$

Any one of these binding constants, i.e., $k_a$, $k_d$ or $K_D$, conceivably can be employed to assess or compare "binding affinity", i.e., the tendency or strength of binding. However, generally as described herein, binding affinity refers to $K_D$.

"CDR" is used herein to refer to a "complementarity determining region" within an analyte-binding molecule or antibody variable sequence. In antibodies, are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact analyte (e.g., antigen) binding. The methods used herein may utilize CDRs defined according to any of these systems, although certain embodiments use Kabat- or Chothia-defined CDRs.

"Component," "components," and "at least one component," refer generally to a capture antibody, a detection or conjugate antibody, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient serum sample, in accordance with the methods described herein and other methods known in the art. Some components can be in solution or lyophilized for reconstitution for use in an assay.

As used herein, the term "conjugate" means an entity comprising a binding pair member and a label.

"Control" refers to a composition known to not contain analyte ("negative control"), or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Epitope," "epitopes," or "epitopes of interest" refer to a site(s) on any analyte that is recognized and can bind to a complementary site(s) on its specific binding partner (e.g., analyte-binding molecule, e.g., antibody or fragment thereof). The analyte and antigen-binding molecule are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an analyte-binding molecule (e.g., antibody or analyte-reactive fragment thereof).

"Flag value" is a threshold or cut-off value that governs whether the signal from the analyte-binding molecule with relatively higher binding affinity for the analyte or a ratio of the signals from both analyte-binding molecules with relatively lower and higher binding affinities for the analyte are used in determining the concentration of analyte in a test sample. Flag value is determined as described herein. It is important to note that the flag value also provides important assay information in and of itself. For example, the flag value can be used in a one-step assay to determine if an assay measured value or portion of a binding curve is falsely decreased due to a hook effect.

As used herein, the term "intensity" means the amount or degree of strength of electricity, light, heat, or sound per unit area or volume. In varying embodiments, the term "intensity" refers to the number of photons counted per unit of area per unit of time. For example, 1000 photons per unit area may be recorded as 500 counts in a single pixel, while 80 photons per unit area are recorded as 40 counts in a single pixel. The particular conversion depends on the detection system used. Intensity is proportional to the number of photons counted.

"Label" and "detectable label" mean a moiety attached, directly or indirectly, to an analyte-binding molecule (e.g., antibody or analyte-reactive fragment thereof) or an analyte to render the reaction between the analyte-binding molecule (e.g., antibody or analyte-reactive fragment thereof) and the analyte detectable, and the an analyte-binding molecule (e.g., antibody or analyte-reactive fragment thereof) or analyte so labeled is referred to as "detectably-labeled." A label can produce a signal that is detectable, e.g., by visual or instrumental means. In this aspect, a label can be any signal-generating moiety, and sometimes is referred to herein as a reporter group. As used herein, the label (or signal-generating moiety) produces a measurable signal which is detectable by external means, e.g., by the measurement of electromagnetic radiation, and, depending on the system employed, the level of signal can vary to the extent the label is in the environment of the solid support, e.g., an electrode, microparticle or bead. Various labels include signal-producing substances, such as enzymes (horseradish peroxidase, alkaline phosphatase, alkaline peroxidase, glucose 6-phosphate dehydrogenase, and the like), chromophores or chromogens (e.g., dyes that absorb light in the ultraviolet or visible region, phosphors, fluorescers, fluorophores (e.g., fluorescent proteins (green fluorescent protein, yellow fluorescent protein, red fluorescent protein, cyan fluorescent protein); phycobilins (phycoerythrin, R-Phycoerythrin, B-Phycoerythrin); Xanthene derivatives (fluorescein, rhodamine, Oregon green, eosin, Texas red); cyanine derivatives (cyanine, Cy dyes, indocarbocyanine, oxacarbocyanine, thiacarbocyanine, merocyanine); naphthalene derivatives (dansyl and prodan derivatives); coumarin derivatives; oxadiazole derivatives (pyridyloxazole, nitrobenzoxadiazole, benzoxadiazole); Pyrene derivatives (cascade blue); oxazine derivatives (Nile red, Nile blue, cresyl violet, oxazine 170); acridine derivatives (proflavin, acridine orange, acridine yellow); arylmethine derivatives (auramine, crystal violet, malachite green); tetrapyrrole derivatives (porphin, phtalocyanine, bilirubin)), luminophores, chemiluminescent compounds, radioactive compounds, and the like). Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. For example, enzymes can be employed to produce a signal or to amplify a signal or both of the foregoing. As another example, the moiety may be a so-called quencher or an entity upon which a quencher acts. Use of the term "detectably-labeled" is intended to encompass these, and other means, of such labeling.

"Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a human suspected of having, diagnosed as having, or undergoing prophylactic or therapeutic treatment for an analyte deficiency or the presence or excess of analyte.

"Patient sample", "Sample," "test sample," and may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. In the context of the present disclosure, the sample is preferably serum or plasma and most preferably serum.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte-binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Quality control reagents" in the context of assays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

"Specific binding partner" is a member of a specific binding pair. A specific binding pair comprises two different molecules, which specifically bind to each other through chemical or physical means. Therefore, in addition to analyte/analyte-binding molecules, and antigen/antibody specific binding pairs of common assays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Specific" and "specificity" in the context of an interaction between members of a specific binding pair (e.g., an antigen (or a fragment thereof) and an antibody (or antigenically reactive fragment thereof)) refer to the selective reactivity of the interaction. The phrase "specifically binds to" and analogous phrases refer to the ability of a first member of a specific binding pair (e.g., an antibody or antigenically reactive fragment thereof) to bind to a second member of a specific binding pair (e.g., an antigen) and not bind specifically to other antigens (or fragments thereof). In the context of the present disclosure an antibody that specifically binds to analyte is considered specific for analyte "Tracer" refers to an analyte or analyte fragment attached to a label, wherein the analyte attached to the label can effectively compete with the analyte for sites on an analyte binding molecule specific for the analyte.

The above terminology is provided for the purpose of describing particular embodiments. The terminology is not intended to be limiting.

1. Introduction

Generally, the assays and methods described herein entail employing three analyte-binding molecules in a sandwich assay (two analyte-binding molecules are used in conventional sandwich assay) to eliminate "hook effect" in a one-step sandwich assay and to expand linear assay dynamic range in a two-step sandwich assay. Such assays and methods also can employed, as newly described herein, to expand the dynamic range in competitive assay format. Two of the three analyte-binding molecules can be used either for capture or detection, but their binding affinity should be different, e.g., as further described herein, and the first and second analyte-binding molecules bind to the third analyte-binding molecule via the analyte independently. When used as capture analyte-binding molecules, in some embodiments, the first and second analyte-binding molecules can be attached to different types of microparticles or on different locations on a surface (e.g., two distinct and spatially separated electrodes). When used as detection analyte-binding molecules, in some embodiments, the first and second analyte-binding molecules can have labels with distinguishable spectroscopic properties (e.g. lifetime, spectral). In both cases, signals generated from the first and second analyte-binding molecules can be measured separately based on their spatial and/or spectroscopic properties. The ratio of signal obtained from the first and second analyte-binding molecules can also be used as an indicator to choose the correct section of the calibration curve. In the two-step sandwich and competitive formats, antibodies with different affinities are attached to different solid supports, and signals from each solid support can be measured independently.

Figure 6A:
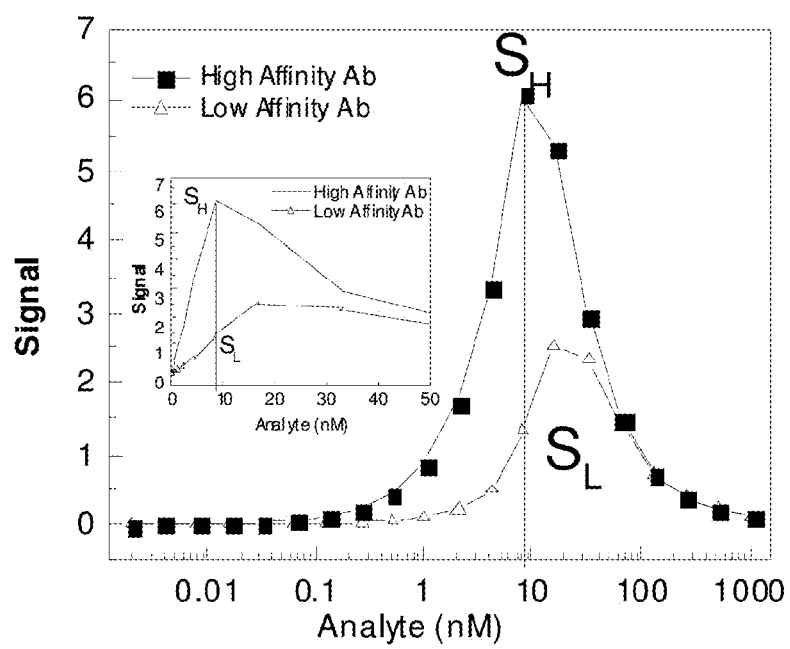
FIGS. 6A-B provide an example of a one-step sandwich assay.
Figure 6B:
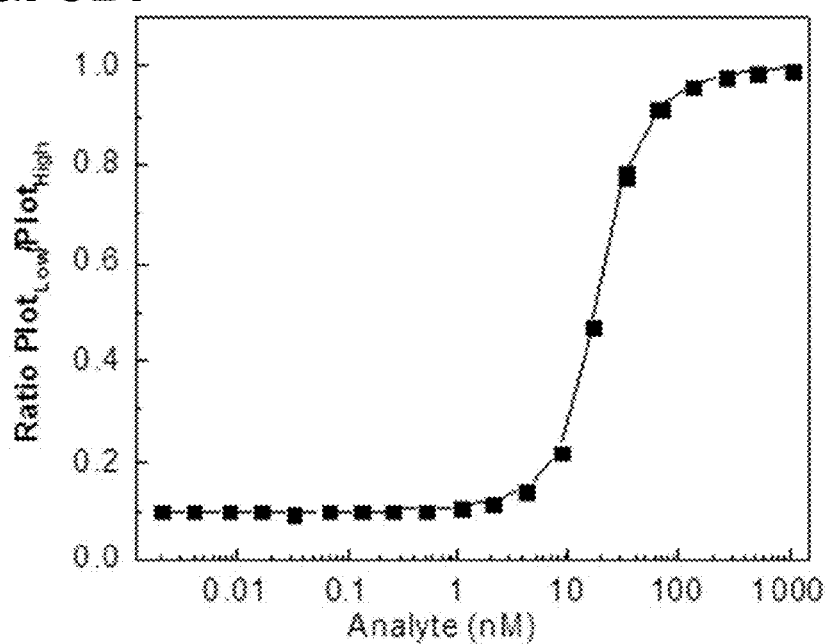

In one-step sandwich assay formats, for a given calibrator set, two calibration plots measuring binding intensity of analyte-binding molecule over a range of analyte concentrations are independently obtained. An analyte-binding molecule of relatively higher binding affinity for the analyte of interest is used as capture agent or detection agent to obtain $Plot_{high}$. An analyte-binding molecule of relatively lower binding affinity for the analyte of interest is used as capture agent or detection agent to obtain $Plot_{low}$. Due to the hook effect, both plots will have a maximal intensity peak (typically at the inflection point), a rising section and a sinking section. A predetermined flag value can be used to determine which section of the curve to use as the calibration curve. The flag value is determined as described herein. $Plot_{high}$ reaches its maximum intensity at a lower analyte concentration. $Plot_{high}$ can also be referred to as the "calibration plot." $Plot_{low}$ reaches its maximum intensity at a higher analyte concentration. The ratio value of the $Plot_{low}$/$Plot_{high}$ at the peak of $Plot_{high}$ is assigned as flag value (See, for example, FIG. 6a). When the ratio of signal intensities $S_L/S_H$ (signal from low affinity molecule/signal from high affinity molecule) in the test sample measurement is less than the predetermined flag value, then the rising section of the calibration curve is used for assay calibration. When the ratio of signal intensities $S_L/S_H$ is higher than the flag value, then the sinking section of the calibration curve is used for assay calibration.

Inverse ratios can also be applied. Conversely, in embodiments of the method where the flag value is determined by dividing $Plot_{high}$ with $Plot_{low}$ at the peak of $Plot_{high}$, when the ratio of signal intensities $S_H/S_L$ (signal from high affinity molecule/signal from low affinity molecule) in the test sample measurement is greater than the flag value, the rising section of the calibration curve is used for assay calibration. Alternatively, when the ratio of signal intensities $S_H/S_L$ in the test sample measurement is equal to or less than the flag value the sinking section of the calibration curve is used for assay calibration.

In the two-step assay, both the high-affinity and low-affinity analyte-binding molecules must be attached to the solid support (e.g., to allow for one or more wash steps). For two-step sandwich assay formats, the signal from the relatively higher binding affinity analyte-binding molecule attached to a solid support plateaus at a higher analyte concentration, while the signal from the low affinity analyte-binding molecule attached to a solid support responds linearly to higher analyte concentration. Therefore, signal from the relatively higher affinity analyte-binding molecule can be used for low analyte concentration measurement, it assures the sensitivity of the assay; while signal from the relatively lower affinity analyte-binding molecules can be used for high analyte concentration measurement. The flag value can be the plateau signal from the relatively higher affinity analyte-binding molecule. For a test sample, if its signal from the relatively higher affinity analyte-binding molecule is equal to or higher than the flag value, then the signal plot from the relatively lower affinity analyte-binding molecules will be used. The relatively higher affinity analyte-binding molecule assures the sensitivity of the assay while the relatively lower affinity analyte-binding molecules expand the assay dynamic range.

Figure 9:
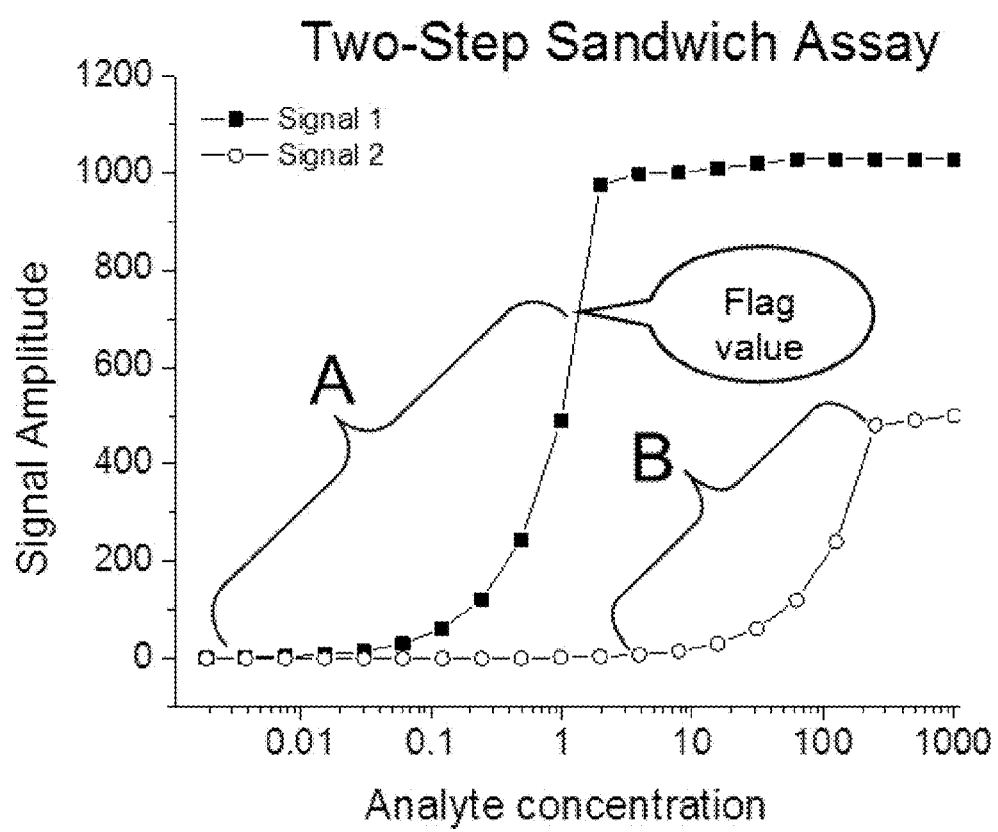
FIG. 9 shows a representative calibration curve generated as a result of a two-step assay carried out as described herein. Signal 1 is originated from the labeled analyte-binding molecules bound to the analyte, which is also bound to the first analyte-binding molecules coated on a first solid support. Signal 2 is originated from the labeled analyte-binding molecules bound to the analyte, which is also bound to the second analyte-binding molecules coated on a second solid support. The regions in the bracket (rising section "A" of the left calibration curve and rising section "B" of the right calibration curve) can be used to determine the concentration value of test samples.

This is depicted in FIG. 9. As can be seen from this figure, the calibration curve for the higher affinity analyte-binding molecule is the curve on the left, and the calibration curve for the lower affinity analyte-binding molecule is the curve on the right. This relationship between the two curves can be employed to establish criteria to select appropriate sections of the signal plots to use for calibrating an assay. In some embodiments, a flag value can be set close to the plateau value of the signal intensity from the first solid support. For a test sample, if signal from first solid support is equal to or higher than the flag value, then the rising section of the signal plot from the second solid support (right side curve, section B) will be used for calibration. Using this approach, it can expand the assay dynamic range.

For competitive assay formats, the signal from the relatively higher affinity analyte-binding molecule attached to a solid support will level off at higher analyte concentration, while the signal from the relatively lower affinity analyte-binding molecule attached to a solid support responds inversely to higher analyte concentration. Therefore signal from the relatively higher affinity analyte-binding molecule can be used for low analyte concentration measurement, it assures the sensitivity of the assay; while signal from the relatively lower affinity analyte-binding molecules can be used for high analyte concentration measurement. The flag value can be the plateau signal from the relatively higher affinity analyte-binding molecule. For a test sample, if signal from the relatively higher affinity analyte-binding molecule is equal to or less than the flag value, then the signal plot from the relatively lower affinity analyte-binding molecules will be used. The relatively higher affinity analyte-binding molecule assures the sensitivity of the assay while the relatively lower affinity analyte-binding molecules expand the assay dynamic range.

Figure 10:
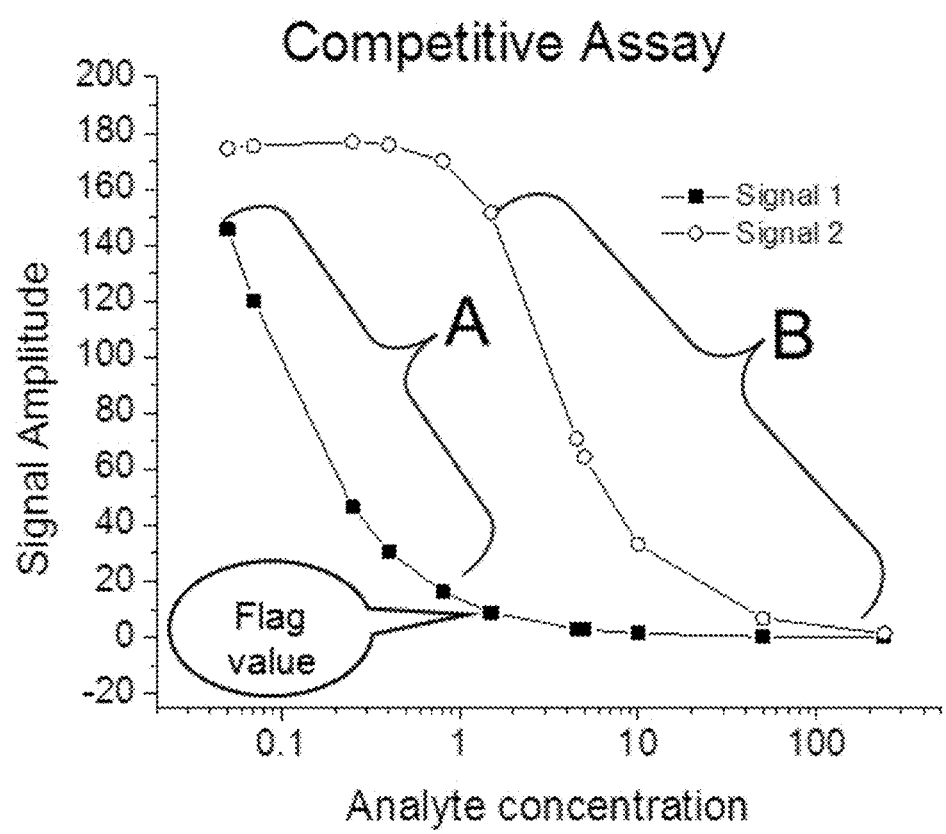
FIG. 10 shows a representative calibration curve generated as a result of a competitive assay carried out as described herein. Signal 1 is originated from the tracer bound to the first analyte-binding molecules coated on the first solid support. Signal 2 is originated from the tracer bound to the second analyte-binding molecules coated on the second solid support. The regions in the bracket (sinking section "A" of the left calibration curve and sinking section "B" of the right calibration curve) can be used to determine the concentration value of test samples.

This is depicted in FIG. 10. As can be seen from this figure, the calibration curve for the higher affinity analyte-binding molecule is the curve on the left, and the calibration curve for the lower affinity analyte-binding molecule is the curve on the right. This relationship between the two curves can be employed to establish criteria to select appropriate sections of the signal plots to use for calibrating an assay. In some embodiments, a flag value can be set close to the leveling off value of the signal intensity from the first solid support. For a test sample, if signal from first solid support is equal to or less than the flag value, then the signal plot from the second solid support (sinking section, curve on right, section B) will be used for calibration. Using this approach, it can expand the assay dynamic range.

It is important to note that by using two analyte-binding molecules with different affinities and/or different concentrations in both the two-step and competitive assay formats, it is possible to obtain well-separated signal plots and thus extend the assay dynamic range.

2. Kits

Kits for assaying a test sample for analyte (or a fragment thereof) are provided herein. In varying embodiments the kits comprise first, second and/or third analyte-binding molecules useful together for assaying the test sample for an analyte of interest and instructions for assaying the test sample for analyte. In varying embodiments, the kits can comprise:

i) a first analyte-binding molecule attached to a first label and a second analyte-binding molecule comprising a second label, wherein the binding affinity for the analyte of the first analyte-binding molecule is greater than that of the second analyte-binding molecule, wherein the first label and the second label are detectably distinguishable (e.g., emit light at detectably distinguishable wavelengths); and a third analyte-binding molecule attached to a solid support, wherein the first analyte-binding molecule and the second analyte-binding molecule do not concurrently bind to the analyte, and the first analyte-binding molecule and the second analyte-binding molecule independently bind to the analyte and, thereby, to the third analyte-binding molecule to form an assay sandwich; or ii) a first analyte-binding molecule attached to a first solid support and a second analyte-binding molecule attached to a second solid support, wherein the first analyte-binding molecule and the second analyte-binding molecule have different binding affinities for the analyte, wherein the first solid support and the second solid support can be distinguished (e.g., by spatial separation, color, shape, size, etc.); and a third analyte-binding molecule attached to a label, wherein the first analyte-binding molecule and the second analyte-binding molecule do not concurrently bind to the analyte, and the first analyte-binding molecule and the second analyte-binding molecule independently bind to the analyte and, thereby, to the third analyte-binding molecule to form an assay sandwich; or iii) a first analyte-binding molecule attached to a first solid support and a second analyte-binding molecule attached to a second solid support, wherein the first analyte-binding molecule and the second analyte-binding molecule have different binding affinities for the analyte, wherein the first solid support and the second solid support can be distinguished (e.g., by spatial separation, color, shape, size, etc.); and tracer comprised of analyte or analyte fragment attached to reporter group which will compete with analyte in the test sample for the binding to the first and second analyte-binding molecules.

As those of skill in the art understand, the components described below with respect to kits are also useful in the methods described herein. Thus, the following description of solid supports and labels apply equally to the kits and methods described herein.

In varying embodiments, the kit can comprise instructions for assaying the test sample for analyte (or fragments thereof) by an assay described herein, e.g., a microparticle assay or an assay for use in a point-of-care device. The instructions can be in paper form or computer-readable form, such as a disk, CD, DVD, or the like. Alternatively or additionally, the kit can comprise a calibrator or control, e.g., purified, and optionally lyophilized, analyte (or a fragment thereof), and/or at least one container (e.g., tube, microtiter plates or strips, which can be already coated with one or more analyte-binding molecules) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying analyte.

As appropriate or desired, the kit can contain a solid support, for example, an electrode, a microparticle, a magnetic particle, bead, test tube, microtiter plate, cuvette, membrane, scaffolding molecule, film, filter paper, disc or chip. Illustrative solid supports include without limitation, e.g., an electrode, a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, or magnetizable microparticles (e.g., microparticles having ferric oxide or chromium oxide cores and homo- or hetero-polymeric coats and radii of about 1-10 microns)). The substrate can comprise a suitable porous material with a suitable surface affinity to bind a capture agent and sufficient porosity to allow access by a detection agent. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an analyte-binding molecule to the substrate. Irreversible binding, generally by adsorption through hydrophobic forces, of the capture agent to the substrate results; alternatively, a chemical coupling agent or other means can be used to bind covalently the capture agent to the substrate, provided that such binding does not interfere with the ability of the capture agent to bind analyte.

One support suitable for use herein is a microparticle. Microparticles that are suitable for use with the methods described herein include, without limitation, magnetic microparticles. The sizes of microparticles typically range from about 0.1 to about 100 µm. Commercially available microparticles are available in a wide variety of materials, including those made of ceramics, glass, polymers, and metals. Magnetic microparticles suitable for use in the methods described herein are commercially available, e.g., from Agilent Technologies, Santa Clara, Calif. Although the generally accepted definition of 0.1 to 100 µm complements the size definition of nanoparticles, there are other ways to define the size. General acceptance considers microparticles smaller than 100 nm to be nanoparticles. Any microparticle larger than 0.5 µm and anything smaller than 0.5 mm is considered to be a microparticle. In general, the size of microparticles suitable for use with the method described herein must be sufficiently large so that two microparticles can be resolved by the image system selected. The properties of the microparticles suitable for use with the method described herein, such as, for example, color, is a matter of choice. One of ordinary skill in the art can select the properties of the microparticles in order to fulfill requirements imposed by appropriate variations of the method.

Reaction vessels that are suitable for use with the kits and methods described herein include micro-well plates and reservoirs in a point-of-care device. In varying embodiments, the reaction vessel can be of such a character that an image of the capture analyte-binding molecule-analyte-detection analyte-binding molecule complex can be made. In one embodiment, the reaction vessel is transparent to electromagnetic radiation, typically in the ultraviolet and the visible range of the spectrum. Materials that are suitable for making a reaction vessel include glass, and polymeric materials. In one embodiment, the material of the reaction vessel is not auto-fluorescent. However, generally, the particular form or shape of the reaction vessel is not critical.

In some embodiments, the first and second analyte-binding molecules or the third analyte-binding molecule are bound with microparticles, which have been previously coated with streptavidin or biotin (e.g., using Power-Bind™-SA-MP streptavidin-coated microparticles (Seradyn, Indianapolis, Ind.)) or anti-species-specific monoclonal antibodies. If necessary, the substrate can be derivatized to allow reactivity with various functional groups on the capture agent. Such derivatization requires the use of certain coupling agents, examples of which include, but are not limited to, maleic anhydride, N-hydroxysuccinimide, and 1-ethyl-3-(3-dimethylaminopropyl) carbodiimide. If desired, one or more capture agents (e.g. analyte-binding molecules (e.g., antibodies or antigenically active fragments thereof)), each of which is specific for analyte can be attached to solid supports in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828).

In varying embodiments, the first and the second analyte-binding molecules or the third analyte-binding molecule are attached, directly or indirectly, to a detectable label. Illustrative labels include, e.g., fluorophore, radioactive moiety, enzyme, biotin/avidin label, chromophore, chemiluminescent label, or the like. Any suitable detectable label as is known in the art can be used. For example, the detectable label can be a radioactive label (such as $^3$H, $^{125}$I, $^{35}$S, $^{14}$C, $^{32}$P, and $^{33}$P), an enzymatic label (e.g., horseradish peroxidase, alkaline phosphatase, alkaline peroxidase, glucose 6-phosphate dehydrogenase, and the like), a chemiluminescent label (e.g., acridinium esters, thioesters, or sulfonamides; luminol, isoluminol, phenanthridinium esters, and the like), one or more chromophores, e.g., one or more dyes which emit light in the ultraviolet or visible region, phosphors, fluorescers, fluorophores (e.g., fluorescent proteins (green fluorescent protein, yellow fluorescent protein, red fluorescent protein, cyan fluorescent protein); phycobilins (phycoerythrin, R-Phycoerythrin, B-Phycoerythrin); Xanthene derivatives (fluorescein, rhodamine, Oregon green, eosin, Texas red); cyanine derivatives (cyanine, Cy dyes, indocarbocyanine, oxacarbocyanine, thiacarbocyanine, merocyanine); naphthalene derivatives (dansyl and prodan derivatives); coumarin derivatives; oxadiazole derivatives (pyridyloxazole, nitrobenzoxadiazole, benzoxadiazole); Pyrene derivatives (cascade blue); oxazine derivatives (Nile red, Nile blue, cresyl violet, oxazine 170); acridine derivatives (proflavin, acridine orange, acridine yellow); arylmethine derivatives (auramine, crystal violet, malachite green); tetrapyrrole derivatives (porphin, phtalocyanine, bilirubin)), luminophores, chemiluminescers, a fluorescent label (e.g., fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In varying embodiments, the first label or the second label is a phycobilin (e.g., phycoerythrin, R-Phycoerythrin, B-Phycoerythrin). R-Phycoerythrin, or PE, are useful as a fluorescence-based indicator for labeling analyte-binding molecules or other molecules in a variety of applications. R-Phycoerythrin absorbs strongly at about 566 nm with secondary peaks at 496 and 545 nm and emits strongly at 575 nm. R-Phycoerythrin is among the brightest fluorescent dyes ever identified. See, for example, Phycoerythrin—Wikipedia, the free encyclopedia, on the internet at en.wikipedia.org/wiki/Phycoerythrin and R-PHYCOERYTHRIN (PB31), ProZyme Inc., Hayward, Calif., both of which are incorporated herein by reference. In embodiments where the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution.

In some embodiments, the kit can include, or the method can employ reagents for labeling the analyte-binding molecules or reagents for detecting the analyte-binding molecules (e.g., detection analyte-binding molecules) and/or for labeling the analytes or reagents for detecting the analyte. The analyte-binding molecules, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the assay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

3. Assay Formats

The present disclosure provides methods for determining the presence, amount or concentration of analyte (or fragments thereof) in a test sample. Any suitable assay as is known in the art can be used in the method. Examples include, but are not limited to, assay, such as sandwich assay (e.g., including radioisotope detection (radioimmunoassay (RIA)) and enzyme detection (enzyme assay (EIA) or enzyme-linked immunosorbent assay (ELISA) (e.g., Quantikine ELISA assays, R&D Systems, Minneapolis, Minn.)), competitive assays, and others.

Methods well-known in the art for collecting, handling and processing urine, blood, serum and plasma, and other body fluids, are used in the practice of the present disclosure, for instance, when the analyte-binding molecules according to the present disclosure are employed as immunodiagnostic reagents, and/or in a kit for assay of analyte. The test sample can comprise further moieties in addition to the analyte, other analytes of interest, such as e.g., proteins, peptides, polypeptides, oligonucleotides or polynucleotides generally, as well as more specifically, e.g., antibodies, antigens, haptens, hormones, drugs, enzymes, or receptors, along with the illustrative analytes described herein and any other analyte of interest. For example, the sample can be a whole blood sample obtained from a subject. It can be necessary or desired that a test sample, particularly whole blood, be treated prior to assay as described herein, e.g., with a pretreatment reagent. Even in cases where pretreatment is not necessary (for example, most urine samples), pretreatment optionally can be done for mere convenience (e.g., as part of a regimen on a commercial platform). Preferably, the test sample is serum.

The pretreatment reagent can be any reagent appropriate for use with the assay and kits described herein. Sackrison et al., for example, discloses lowering the pH of the sample to 5.5 or less to dissociate analyte from analyte-binding proteins (see, e.g., U.S. Pat. App. Pub. No. 2004/0132104). The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent optionally precipitates antibodies present in the sample. Such a pretreatment step comprises removing any antibodies by separating from the precipitated antibodies the supernatant of the mixture formed by the addition of the pretreatment agent to the sample. In such an assay, the supernatant of the mixture absent any binding protein is used in the assay, proceeding directly to the capture step.

With use of a homogeneous pretreatment reagent there is no such separation step. The entire mixture of test sample and pretreatment reagent are contacted with a labeled analyte-binding molecule specific for analyte (or fragments thereof), such as a labeled antibody or antigenically reactive fragment thereof that specifically binds analyte. The pretreatment reagent employed for such an assay typically is diluted in the pretreated test sample mixture, either before or during capture by the first analyte-binding molecule. Despite such dilution, a certain amount of the pretreatment reagent (for example, 5 M methanol and/or 0.6 M ethylene glycol) is still present (or remains) in the test sample mixture during capture.

In a heterogeneous format, after the test sample is obtained from a subject, a first mixture is prepared. The mixture contains the test sample being assessed for analyte (or fragments thereof) and one or two analyte-binding molecules (e.g., antibodies or antigenically active fragments thereof), wherein the analyte-binding molecules and any analyte contained in the test sample form an analyte-binding molecule-analyte complex. In varying embodiments, the analyte-binding molecules can be first and second antibodies (or fragments thereof) that specifically bind analyte, e.g., antibodies described herein, or other commercially available antibodies. The order in which the test sample and the analyte-binding molecules are added to form the mixture is not critical. In varying embodiments, the analyte-binding molecules are immobilized on a solid support. The solid support used in the assay (for a first analyte-binding molecule and, optionally, a second analyte-binding molecule) can be any solid support known in the art, such as, but not limited to, an electrode, a magnetic particle, a microparticle, a bead, a test tube, a microtiter plate, a cuvette, a membrane, a scaffolding molecule, a film, a filter paper, a disc and a chip.

After the mixture containing the first (and second) analyte-binding molecule-analyte complexes are formed, any unbound analyte is removed from the complex using any technique known in the art. For example, the unbound analyte can be removed by washing. Desirably, however, the analyte-binding molecules are present in excess of any analyte present in the test sample, such that all analyte that is present in the test sample is bound by the analyte-binding molecules.

Figure 4:
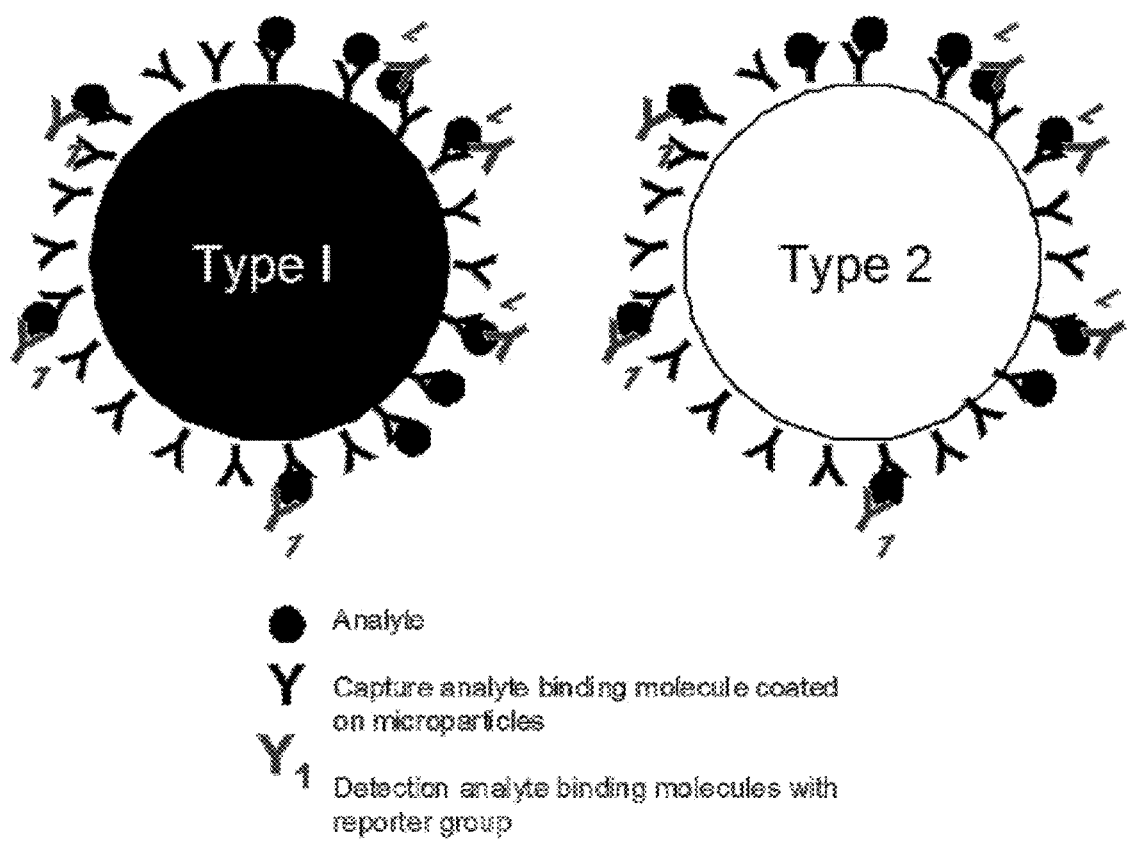
FIG. 4 provides an illustrative diagram of an embodiment of the assay where the first analyte-binding molecule is attached to a first type of solid support, the second analyte-binding molecule is attached to a second type of solid support, and the third analyte-binding molecule is attached to a label.
Figure 5:
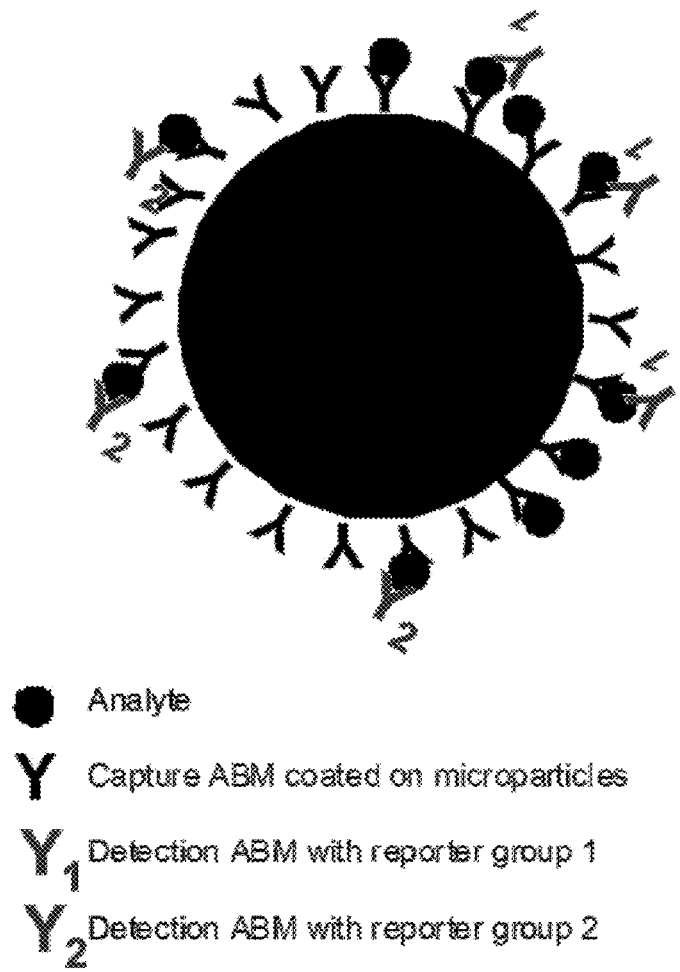
FIG. 5 provides an illustrative diagram of an embodiment of the assay where the first analyte-binding molecule is attached to a first label, the second analyte-binding molecule is attached to a second label, and the third analyte-binding molecule is attached to a solid support. ABM; analyte-binding molecule.

In one assay format, the analyte is mixed with one or two detection analyte-binding molecules and one or two capture analyte-binding molecules attached to solid support, such that a mixture of complexes are formed. The following are examples of the alternate sandwich complexes formed:

i) As shown in FIG. 4, a first sandwich complex is formed by a first analyte-binding molecule attached or bound to a first solid support (e.g., capture analyte-binding molecule coated on microparticles)—analyte—third analyte-binding molecule attached to a label (e.g., detection analyte-binding molecule with reporter group). A second sandwich complex is formed by a second analyte-binding molecule attached or bound to a second solid support—analyte—third analyte-binding molecule attached to a label.

ii) As shown in FIG. 5, a first sandwich complex is formed by a first analyte-binding molecule attached to a first label (e.g., detection analyte-binding molecule with reporter group 1)—analyte—third analyte-binding molecule attached to a solid support (e.g., capture analyte-binding molecule coated on microparticles) and a second sandwich complex formed by a second analyte-binding molecule attached to a second label (e.g., detection analyte-binding molecule with reporter group 2)—analyte—third analyte-binding molecule bound to a solid support.

Generally, a sample being tested for (for example, suspected of containing) analyte (or fragments thereof) can be contacted with at least one capture agent (e.g., analyte-binding molecule (e.g., capture antibody or antigenically reactive fragment thereof)) and at least one detection agent (e.g., detection analyte-binding molecule (e.g., an antibody or antigenically reactive fragment thereof)) either simultaneously or sequentially and in either order. For example, the test sample can be first contacted with at least one capture agent and then (sequentially) with at least one detection agent. Alternatively, the test sample can be first contacted with at least one detection agent and then (sequentially) with at least one capture agent. In yet another alternative, the test sample can be contacted simultaneously with a capture agent and a detection agent.

In the one-step sandwich assay format, a sample suspected of containing analyte (or fragments thereof) is brought into contact with both the one or two types capture analyte-binding molecules and one or two types of the detection analyte-binding molecules under incubation conditions that allow the formation of multiple capture agent/analyte/detection agent complex. The sample, capture agents and detection agent are all added sequentially or simultaneously to a reaction vessel).

In the two-step assay format, a sample suspected of containing analyte (or fragments thereof) is first brought into contact with two types of capture analyte-binding molecules, each attached to a different solid support. After formation of the capture agent/analyte complexes, unbound analyte in the sample are removed from the reaction vessel in a washing step. The complexes are then contacted with at least one detection agent (under conditions which allow for the formation of a capture agent/analyte/detection agent complexes.

In the competitive assay format, a sample suspected of containing analyte (or fragments thereof) is first brought into contact with two types of capture analyte-binding molecules, each attached to a different solid support. After formation of the capture agent/analyte complexes, tracer comprised of analyte (or fragment thereof) with attached reporter group will be added to the reaction mixture to bind all the remaining analyte-binding molecules. The tracer, sample and capture analyte-binding molecules can also be mixed in one step.

In each of these formats, optionally, prior to contacting the test sample with at least one capture agent, at least one capture agent can be bound to a substrate to facilitate separation of the capture agent/analyte complex. The substrate to which the capture agent is bound can be any suitable solid support that facilitates separation of the capture agent/analyte complex from the sample, as described above and herein.

The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes.

If the capture agent/analyte complex are contacted with more than one detection agent, then multiple capture agent/analyte/detection agent complexes are formed. As with the capture agent, when the at least one detection agent is brought into contact with the capture agent/analyte complex, a period of incubation under conditions similar to those described above is required for the formation of the capture agent/analyte/detection agent complex(es). Preferably, at least one detection agent contains a detectable label. The detectable label can be bound to the at least one detection agent prior to, simultaneously with, or after the formation of the capture agent/analyte/detection agent complex(es). Any detectable label known in the art can be used (see discussion above, including Polak and Van Noorden (1997) and Haugland (1996)).

The detectable label can be bound to the detection agent either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to a detection agent are known in the art.

The capture agent/analyte/detection agent complex(es) can be, but do not have to be, separated from the remainder of the test sample prior to quantification of the label. For example, if the at least one capture agent is bound to a solid support, such as a well or a bead, separation can be accomplished by removing the fluid (of the test sample) from contact with the solid support. Alternatively, if the at least one capture agent is bound to a solid support, it can be simultaneously contacted with the test sample and the at least one detection agent to form a capture agent/analyte/detection agent complex(es), followed by removal of the test sample from contact with the solid support. When the assay does not includes a separation of bound from unbound sample analyte it is considered 'one-step' assay. When the assay does include a separation of bound from unbound sample analyte it generally is considered a 'two-step assay' (or delayed one-step assay, depending on how the separation is carried out).

After formation of the capture agent/analyte/detection agent complex(es), the amount of label in the complex(es) is quantified using techniques known in the art. The signal (e.g., color, light, radioactivity, reactive oxygen species) that is generated can be detected using routine techniques known to those skilled in the art. Based on the intensity of the signal generated, the amount of analyte in the sample can be quantified. Specifically, the amount of analyte in the sample is proportional to the intensity of the signal generated. The amounts of analyte present can be quantified by comparing the amount of signal generated to a standard curve for analyte or by comparison to a reference standard. The standard curve can be generated using serial dilutions or solutions of known concentrations of analyte by mass spectroscopy, gravimetric methods, and other techniques known in the art.

For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of analyte in the test sample is determined by use of a calibration curve that has been generated using serial dilutions of a known concentration of analyte.

In varying embodiments, the methods employ microparticle solid supports and are performed using automated or semi-automated systems. Imaging systems suitable for use in the methods described herein can be any system capable of obtaining images such that individual microparticles can be resolved. Imaging devices suitable for use with the method described herein include, but are not limited to, light microscopes, fluorescence imaging scanners, and the like. Such use of imaging systems are described, e.g., in US 20120308997, incorporated by reference for its teachings regarding same. Image file types that are suitable for use with the method described herein include, but are not limited to, JPEG/JFIF, GIF, BMP, TIFF, and FITS. Image file formats are described at Image file formats—Wikipedia, the free encyclopedia, which is accessible by means of Hypertext Transfer Protocol at the website en.wikipedia.org/wiki/image_file_formats, incorporated herein by reference, and FITS is described at FITS—Wikipedia, the free encyclopedia, which is accessible by means of Hypertext Transfer Protocol at the website en.wikipedia.org/wiki/FITS, incorporated herein by reference.

Duration of exposure during acquisition of the image is not critical. Exposure times suitable for use with the method described herein can be any exposure time that provides sufficient resolution for discerning relevant details of the image.

The selection of the region of interest is important. Through the use of a suitable computer program, the locations of individual microparticles are determined by means of contrast or some alternative criteria. The pixels associated with the microparticles or other solid support can be deemed a region of interest. In order to obtain a meaningful value of concentration of an analyte in a sample, typically at least about 100 microparticles, e.g., at least about 200 microparticles are located in an image. Commercially available computer programs suitable for use in the method described herein include, but are not limited to, those programs having the trademarks "SLIDEBOOK" (Intelligent Imaging Innovations, Inc., Denver, Colo.; on the internet at slidebook.com) and "METAMORPH" (Molecular Devices, LLC, Sunnyvale, Calif.) or software in the public domain, such as, for example, ImageJ (on the internet at rsbweb.nih.gov/ij/).

In performing one form of the method, a commercially available epifluorescence microscope can be used to image the complexes through a transparent surface upon which they are supported. A standard epifluorescence microscope, a confocal or TIRF (total internal reflection fluorescence) microscope can be used. In varying embodiments, a TIRF microscope is used because this type of microscope has better z-plane resolution, which can eliminate signals from above the focal plane where the microparticles are positioned, thereby lowering the background signal. A representative example of such a microscope is a motorized inverted fluorescence microscope (OLYMPUS "IX81"; on the internet at olympusamerica.com/) coupled with a high resolution CCD camera (e.g., Hamamatsu Model C4742-80-12AG; on the internet at learn.hamamatsu.com/products). Other comparable microscopes and cameras that find use are commercially available.

In this basic form of the method, a single-color approach can be used to provide greater sensitivity than a conventional assay employing a light signal from the total volume of a reaction mixture. This greater sensitivity can be evidenced by a plot of a linear function having a greater slope at lower concentrations relative to that of a linear plot employed as a calibration curve in a conventional assay.

Microparticles bearing capture analyte-binding molecules, detection analyte-binding molecules attached to fluorophores, and a sample suspected of containing an analyte are combined under appropriate conditions to carry out an assay. After the assay is carried out, any fluorescent light signal that does not emanate from a complex comprising a microparticle attached to a capture analyte-binding molecule, an analyte, and a conjugate comprising a detection analyte-binding molecule attached to a fluorophore is omitted. Then, the complexes remaining are further qualified based on fluorescence emitted by the fluorophore of the conjugate. This latter step omits any sections on the surface of the microparticle that do not meet selection criteria. Based on a statistical parameter, such as, for example, standard deviation, a typical example of a selection criterion is that the microparticles to be used for measurement have a substantially homogeneous coating, which essentially eliminates excessive aggregation of conjugates, which can result from a high degree of non-specific binding. In general, selection criteria vary, depending upon the particular assay. One of ordinary skill in the art of the particular assay should be able to formulate meaningful selection criteria for that particular assay. Finally, the average value of intensity per pixel of the qualified particles is measured in order to compare the intensity to a calibration curve that establishes concentration of the analyte as a function of intensity. The average value of intensity per pixel of the qualified particles can be determined by means of a CCD camera, which is capable of measuring intensity of light. The measurement of intensity is converted to a parameter, which is designated in the units of counts. Each pixel has a number corresponding to the intensity of light measured at that pixel.

In another embodiment, a white light image of the reaction mixture is obtained. The white light image is employed to locate the position of each solid support, e.g., microparticle. A white light image s formed by using the entire electromagnetic spectrum for both illumination and detection. This step is not required, but is useful because it eliminates signals not originating from microparticles. A fluorescence image is then acquired to determine the location and intensity of detection analyte-binding molecules attached to microparticles. The fluorescence image uses a color, e.g., red, green. Counts per pixel are calculated and the average and standard deviation of counts per pixel are recorded. Pixels that have counts greater than or less than, for example, two times the aforementioned standard deviation are omitted from the analysis. The average number of counts per pixel for the pixels remaining is calculated. The quantity of signal measured from the label of the detection analyte-binding molecule determines the concentration of the analyte.

In order to carry out a measurement that will provide a higher degree of sensitivity, a commercially available epifluorescence microscope can be used to image the complexes through a transparent surface upon which they are supported. A representative example of such a microscope is a motorized inverted fluorescence microscope (OLYMPUS "IX81") coupled with a high resolution CCD camera (Hamamatsu Model C4742-80-12AG), which are commercially available from numerous sources.

In this higher sensitivity measurement, a dual-color approach is used to provide greater sensitivity than both a conventional assay employing a light signal from the total volume of reaction mixture and a measurement made by the single-color approach described earlier. This greater sensitivity is evidenced by a plot of a linear function having a greater slope at lower concentrations relative to that of a linear plot employed as a calibration curve in a conventional assay or an assay using the single-color approach. For performing the present methods commercially available instrumentation is adapted to add a second detection channel for detecting the first tripartite complex identified by the first label and a second channel for detecting the second tripartite complex identified by the second label. A fluorescence channel is defined with a set of filters comprising an excitation filter and an emission filter, which allows light having a specific wavelength to reach the sample and a signal having a specific wavelength to reach the CCD camera. For example, the fluorophore PE can only be detected in the PE channel and cannot be detected in any other fluorescence channel. Similarly, the fluorophore Cy5 can only be detected in the Cy5 channel and cannot be detected in any other fluorescence channel. Representative automated and semi-automated systems that can be readily adapted to include a second detection channel, include, e.g., ARCHITECT®, AxSYM®, IMx® PRISM®, EIA (bead), Quantum™ II, and Abbott Point of Care (i-STAT®, Abbott Laboratories).

Microparticles bearing capture analyte-binding molecules, detection analyte-binding molecules attached to fluorophores, and a sample suspected of containing an analyte are combined under appropriate conditions to carry out an assay. After the assay is carried out, any fluorescent light signal that does not emanate from a complex comprising microparticle attached to a capture analyte-binding molecule, an analyte, and a conjugate comprising a detection analyte-binding molecule attached to a first fluorophore is omitted. Next, an image of the capture analyte-binding molecule (characterized by a second fluorophore, which is different from the first fluorophore) is obtained. This image omits any pixels corresponding to any microparticles that are not coated with capture analyte-binding molecule in a homogeneous manner. If a microparticle is not uniformly coated, pixels from that part are omitted. Then, the complex is further qualified based on fluorescence emitted by the conjugate. This latter step omits any sections on the complex that do not meet selection criteria. A typical example of a selection criterion is homogeneous coating, which essentially eliminates excessive aggregation of conjugates, which can result from a high degree of non-specific binding. As stated previously, selection criteria vary, depending upon the particular assay. Finally, the average value of intensity per pixel of the qualified particles is measured in order to compare the intensity to a calibration curve that establishes concentration of the analyte.

In another embodiment, a white light image of the sample is obtained. The white light image is employed to determine the location of microparticles. This step is not required, but is useful because it may be desirable to locate the position of each solid support, e.g., microparticle. A first fluorescence image is then acquired to determine the locations of the capture analyte-binding molecules attached to microparticles. The first fluorescence image uses a color, e.g., red, green. A second fluorescence image is acquired to determine the locations of analyte-binding molecules that are present as a component of a conjugate. The second fluorescence image uses a color, e.g., red, green, but the color of the second fluorescent image differs from the color of the first fluorescent image. Pixels derived from both a capture analyte-binding molecule on a microparticle and an analyte-binding molecule on a conjugate are selected for further analysis. Counts per pixel are calculated and the average and standard deviation of counts per pixel are recorded. Pixels that have counts greater than or less than, for example, two times the standard deviation calculated are omitted from the analysis. The average number of counts per pixel for the pixels remaining is calculated. The quantity of signal measured from the label of the detection analyte-binding molecule determines the concentration of the analyte.

4. Adaptation of Kits and Methods for Particular Instruments

The concepts, kits and methods as described herein can be implemented on any system or instrument, including any manual, automated or semi-automated systems. The following adaptations are included as merely exemplary.

The kit (or components thereof), as well as the methods of determining the concentration of analyte in a test sample by an assay as described herein, can be adapted for use in a variety of automated and semi-automated systems (including those wherein the solid support comprises an electrode or a microparticle). Illustrative automated and semi-automated systems are described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the capture analyte-binding molecule(s) (e.g., capture analyte-binding molecule, e.g., antibody or antigenically active fragments thereof) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection analyte-binding molecule(s) (e.g., detection analyte-binding molecule, e.g., antibody, or antigenically active fragments thereof) such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical assay system that performs sandwich assays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is useful. A microfabricated silicon chip is manufactured with a pair of gold amperometric working electrodes and a silver-silver chloride reference electrode. On one of the working electrodes, polystyrene beads (0.2 mm diameter) with immobilized high affinity capture analyte-binding molecule(s) are adhered to a polymer coating of patterned polyvinyl alcohol over the electrode. The immobilized lower affinity capture analyte-binding molecule(s) are adhered to the second electrode. This chip is assembled into an I-STAT® cartridge with a fluidics format suitable for assay. On a portion of the wall of the sample-holding chamber of the cartridge there is a layer comprising the detection analyte-binding molecule(s) labeled with alkaline phosphatase (or other label). Within the fluid pouch of the cartridge is an aqueous reagent that includes p-aminophenol phosphate.

In operation, a sample containing analyte is added to the holding chamber of the test cartridge and the cartridge is inserted into the I-STAT® reader. After the detection analyte-binding molecule(s) (e.g., detection analyte-binding molecule, e.g., antibody or antigenically active fragment thereof) has dissolved into the sample, a pump element within the cartridge forces the sample into a conduit containing the chip. Here it is oscillated to promote formation of the sandwich between the capture analyte-binding molecule(s), analyte, and the labeled detection analyte-binding molecule(s). In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte in the sample by means of an embedded algorithm and factory-determined calibration curve.

It further goes without saying that the methods and kits as described herein necessarily encompass other reagents and methods for carrying out the assay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-STAT® cartridge format, using a nucleic acid sequence linked to the signal or detection analyte-binding molecule as a signal amplifier.

Generally, for use with the present kits and methods, automated and semi-automated systems are adapted to analyze samples using two different channels, a first channel for detecting the first tripartite complex identified by the first label and a second channel for detecting the second tripartite complex identified by the second label.

Generally, the present kits and methods can be employed for any purpose, e.g., for diagnosing, prognosticating, or assessing the efficacy of therapeutic/prophylactic treatment of a patient, among other uses.

5. Analytes

The kits and methods provided herein are useful for detecting any analyte of interest. Illustrative analytes of interest include without limitation, e.g., proteins, peptides, polypeptides, oligonucleotides or polynucleotides generally, as well as more specifically, e.g., antibodies, antigens, haptens, hormones, drugs, enzymes, or receptors. As appropriate, commercially available analyte-binding molecules (e.g., antibodies or antigenically reactive fragments thereof) can be used in the presently described kits and assays, or analyte-binding molecules (e.g., antibodies or antigenically reactive fragments thereof) can be generated using methods known in the art. Generally, analytes detected using the herein described kits and methods can be detected by sandwich assay.

Illustrative analytes of interest to be detected using the present kits and assay methods include without limitation, e.g., cytokines, immunosuppressant drugs, cardiovascular disease antigens, cancer antigens, infectious disease antigens, pharmacologic agents, hormones, plasma, serum and/or blood antigens, biomarkers (e.g., for kidney injury), vitamins and autoimmune antigens. Such analytes include but are not limited to e.g.: cytokines, immunosuppressant drugs (e.g., sirolimus, tacrolimus, everolimus, temsorolimus, zotarolimus, cyclosporine, or analogs of any of these compounds); cardiovascular disease antigens (e.g., troponin I, cardiac troponin I (cTnI), serum creatine kinase MB isozyme (CKMB), Basic or B-type natriuretic peptide (BNP), galectin-3, myeloperoxidase (MPO), myoglobin, D-dimer fibrin degradation product (or FDP), high sensitivity C-reactive protein); cancer antigens (e.g., prostate-specific antigen (PSA), alfa-fetoprotein (AFP), CA 125, CA 15-3, CA 19-9, CA 19-9 XR, Carcinoembryonic antigen (CEA), cytokeratin 19, cytokeratin fragment 21-1 (CYFRA. 21-1), Human epididymis protein 4 (HE4), Progastrin-releasing peptide (ProGRP), Squamous cell carcinoma antigen (SCC-Ag)); infectious disease antigens (e.g., cytomegalovirus (CMV) IgG, CMV IgM, Rubella IgG, Rubella IgM, *Toxoplasma* IgG, *Toxoplasma* IgM, Hepatitis A virus (HAV) IgG, HAV IgM, Hepatitis B core protein (HBc), HBc IgM, hepatitis B surface antigen (HBsAg), hepatitis B e antigen (HBeAg), Hepatitis C Virus (HCV, human immunodeficiency virus (HIV)), Chagas, Epstein Barr Virus (EBV), syphilis, Human T-lymphotropic virus (HTLV), Antistreptolysin O (ASO)); pharmacologic agents (e.g., Acetaminophen, Amphetamine/Methamphetamine, Barbiturates, Benzodiazepines, Cannabinoids, Cocaine, Ecstasy, Ethanol, Methadone, Opiates, Phencyclidine (PCP), Propoxyphene, Salicylate, Tricyclic Antidepressants, Amikacin, Carbamazepine, Digitoxin, Digoxin, Gentamicin, Lithium, Phenobarbital, Phenytoin, Quinidine, Theophylline, Tobramycin, Valproic Acid, Vancomycin); hormones (e.g., Dehydroepiandrosterone sulfate (DHEA-S), Estradiol, follicle stimulating hormone (FSH), human chorionic gonadotropin (hCG), luteinizing hormone (LH), Progesterone, Prolactin, Sex hormone-binding globulin (SHBG), Testosterone, cortisol, insulin, pepsinogen I, pepsinogen II, C-peptide, Parathyroid hormone (PTH), thyroid hormone T3, thyroid hormone T4, thyroid stimulating hormone), enzymes (e.g., Acid Phosphatase, Alanine Aminotransferase, Alkaline Phosphatase, Amylase, Aspartate Aminotransferase, Creatine Kinase, Gamma-Glutamyl Transferase (GGT), Lactate Dehydrogenase (LDH), a hydroxybutyrate dehydrogenase (a HBDH), Lipase; Cholinesterase, Ceruloplasmin); plasma, serum and/or blood antigens (e.g., Albumin, microalbumin, prealbumin, Creatinine, Cystatin C, Bilirubin, Lipoprotein(a) [Lp (a)], low density lipoprotein (LDL), high density lipoprotein (HDL), Apolipoprotein A1, Apolipoprotein B, Complement C3, Complement C4, Haptoglobin, Immunoglobulin A (IgA), Immunoglobulin E (IgE), Immunoglobulin G (IgG), Immunoglobulin M (IgM), Kappa Light Chain, Lambda Light Chain, Beta2 Microglobulin, hemoglobin, homocysteine, C-reactive protein (CRP)); biomarkers (e.g., for kidney injury, e.g., neutrophil gelatinase-associated lipocalin (NGAL)); vitamins (e.g., vitamin B12, folate, vitamin D); Anti-cyclic citrullinated peptide (anti-CCP) antibody, Alpha-1 antitrypsin (AAT), Alpha-1 Glycoprotein, autoimmune antigens (e.g., Rheumatoid Factor (RF), Anti-Thyroglobulin (Anti-Tg), and Anti-thyroid peroxidase antibodies (anti-TPO antibodies)).

6. Tracer Analytes

In varying embodiments, the tracer analyte employed in competitive assays is the analyte of interest, or a fragment or mimetic thereof, that can form a complex with a capture analyte-binding molecule and a detection analyte-binding molecule in a sandwich assay. As appropriate, protein analytes can be purified from natural sources or produced by recombinant or synthetic means, as described herein and known in the art. Non-protein analytes can be produced by chemical and synthetic (including biosynthetic) means known to those of skill in the art. The tracer analyte can be attached directly or indirectly to a label.

The label can be any detectable label, as described herein. Illustrative labels include, e.g., fluorophore, radioactive moiety, enzyme, biotin/avidin label, chromophore, chemiluminescent label, or the like. Any suitable detectable label as is known in the art can be used. For example, the detectable label can be a radioactive label (such as $^3$H, $^{125}$I, $^{35}$S, $^{14}$C, $^{32}$P, and $^{33}$P), an enzymatic label (e.g., horseradish peroxidase, alkaline phosphatase, alkaline peroxidase, glucose 6-phosphate dehydrogenase, and the like), a chemiluminescent label (e.g., acridinium esters, thioesters, or sulfonamides; luminol, isoluminol, phenanthridinium esters, and the like), one or more chromophores, e.g., one or more dyes which emit light in the ultraviolet or visible region, phosphors, fluorescers, fluorophores (e.g., fluorescent proteins (green fluorescent protein, yellow fluorescent protein, red fluorescent protein, cyan fluorescent protein); phycobilins (phycoerythrin, R-Phycoerythrin, B-Phycoerythrin); Xanthene derivatives (fluorescein, rhodamine, Oregon green, eosin, Texas red); cyanine derivatives (cyanine, Cy dyes, indocarbocyanine, oxacarbocyanine, thiacarbocyanine, merocyanine); naphthalene derivatives (dansyl and prodan derivatives); coumarin derivatives; oxadiazole derivatives (pyridyloxazole, nitrobenzoxadiazole, benzoxadiazole); Pyrene derivatives (cascade blue); oxazine derivatives (Nile red, Nile blue, cresyl violet, oxazine 170); acridine derivatives (proflavin, acridine orange, acridine yellow); arylmethine derivatives (auramine, crystal violet, malachite green); tetrapyrrole derivatives (porphin, phtalocyanine, bilirubin)), luminophores, chemiluminescers, a fluorescent label (e.g., fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, quantum dots (e.g., zinc sulfide-capped cadmium selenide), a thermometric label, or an immuno-polymerase chain reaction label. In varying embodiments, the tracer analyte is labeled with a phycobilin (e.g., phycoerythrin, R-Phycoerythrin, B-Phycoerythrin). In some embodiments, the tracer analyte is labeled with an acridinium compound, e.g., acridinium-9-carboxamide, at least one acridinium-9-carboxylate aryl ester, or any combination thereof.

7. Analyte-Binding Molecules

Generally, the kits and assays described herein employ three analyte-binding molecules, wherein two of the three analyte-binding molecules compete for complexing with the analyte and the third analyte-binding molecule. The analyte-binding molecules that compete for complexing with the analyte and the third analyte-binding molecule bind the analyte with different affinities, e.g., from about 3-fold to about 5-fold, from about 5-fold to about 100-fold, from about 5-fold to about 10-fold, from about 5-fold to about 25-fold, from about 25-fold to about 50-fold, from about 50-fold to about 100-fold, with about 3-fold, about 5-fold, about 10-fold, about 25-fold, about 50-fold, about 100-fold, or more-fold differences in affinities for binding to the analyte. In varying embodiments, one or two of the analyte-binding molecules are bound directly or indirectly to a label. In varying embodiments, one, two or three of the analyte-binding molecules are antibodies or antigenically reactive fragments (i.e., that bind analyte) thereof.

In some embodiments, one, two or three of the analyte-binding molecules are non-antibody analyte-binding molecules. Other compounds have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (Proc. Natl. Acad. Sci. U.S.A. 92(14):6552-6556 (1995)) discloses an alternative to antibodies based on cytochrome b562. Ku et al. (1995) generated a library in which two of the loops of cytochrome b562 were randomized and selected for binding against bovine serum albumin. The individual mutants were found to bind selectively with BSA similarly with anti-BSA antibodies.

Lipovsek et al. (U.S. Pat. Nos. 6,818,418 and 7,115,396) discloses an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted analyte. Any technique for evolving new or improved binding proteins can be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are therefore, stable under conditions which would normally break down antibodies. In addition, since the structure of these fibronectin-based antibody mimics is similar to that of the IgG heavy chain, the process for loop randomization and shuffling can be employed in vitro that is similar to the process of affinity maturation of antibodies in vivo.

Beste et al. (Proc. Natl. Acad. Sci. U.S.A. 96(5): 1898-1903 (1999)) discloses an antibody mimic based on a lipocalin scaffold (Anticalin®). Lipocalins are composed of a β-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Anticalins® are small, single chain peptides, typically between 160 and 180 residues, which provide several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene with respect to each other. Because of this geometric confirmation, all of the loops are available for binding, increasing the binding affinity to an analyte. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (Cell. Mol. Biol. 49(2):209-216 (2003)) discusses a methodology for reducing antibodies into smaller peptidomimetics, they term "antibody like binding peptidomemetics" (ABiP) which can also be useful as an alternative to antibodies.

Silverman et al. (Nat. Biotechnol., 23: 1556-1561 (2005)) discloses fusion proteins that are single-chain polypeptides comprising multiple domains termed "avimers." Developed from human extracellular receptor domains by in vitro exon shuffling and phage display the avimers are a class of binding proteins somewhat similar to antibodies in their affinities and specificities for various target molecules. The resulting multidomain proteins can comprise multiple independent binding domains that can exhibit improved affinity (in some cases sub-nanomolar) and specificity compared with single-epitope binding proteins. Additional details concerning methods of construction and use of avimers are disclosed, for example, in U.S. Patent App. Pub. Nos. 2004-0175756, 2005-0048512, 2005-0053973, 2005-0089932 and 2005-0221384.

Oftentimes, commercially available antibodies or analyte-binding molecules can be used in the present assays. In varying embodiments, one, two or three of the analyte-binding molecules is generated, e.g., using known recombinant and/or monoclonal antibody production techniques.

Monoclonal antibodies can be produced and modified (e.g., conservatively substituted) in accordance with methods known in the art. The ability of a modified antibody, or antigenically reactive fragment thereof, to detect analyte can be determined using any standard method known in the art for assessing antigen binding specificity, including, for example, the methods described and exemplified herein. Such methods include, but are not limited to, ELISA, Western blot, surface plasmon resonance (e.g., BIAcore®), KinExA® (Kinetic Exclusion Assay) assay, and radioimmunoassay. Preferably, the modified antibody, or antigenically reactive fragment, demonstrates analyte binding characteristics that are at least as good as, and preferably (even desirably) better than, the corresponding unmodified antibody.

a. Synthetic Production

Once sequenced, polypeptides, such as a monoclonal antibody (or a fragment thereof), which specifically binds analyte, can be synthesized using methods known in the art, such as, for example, exclusive solid support synthesis, partial solid support synthesis, fragment condensation, and classical solution synthesis. See, e.g., Merrifield, J. Am. Chem. Soc. 85: 2149 (1963). On solid support, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories (Richmond, Calif.), and the preparation of the hydroxymethyl resin is described by Bodonszky et al., Chem. Ind. (London) 38: 1597 (1966). The benzhydrylamine (BHA) resin has been described by Pietta and Marshall, Chem. Comm. 650 (1970) and is commercially available from Beckman Instruments, Inc. (Palo Alto, Calif.) in the hydrochloride form. Automated peptide synthesizers are commercially available, as are services that make peptides to order.

Thus, the polypeptides can be prepared by coupling an alpha-amino protected amino acid to the chloromethylated resin with the aid of, for example, cesium bicarbonate catalyst, according to the method described by Gisin, Helv. Chim. Acta. 56: 1467 (1973). After the initial coupling, the alpha-amino protecting group is removed by a choice of reagents including trifluoroacetic acid (TFA) or hydrochloric acid (HCl) solutions in organic solvents at room temperature.

Suitable alpha-amino protecting groups include those known to be useful in the art of stepwise synthesis of peptides. Examples of alpha-amino protecting groups are: acyl type protecting groups (e.g., formyl, trifluoroacetyl, and acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, and cyclohexyloxycarbonyl), and alkyl type protecting groups (e.g., benzyl and triphenylmethyl). Boc and Fmoc are useful protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride and dimethyl formamide (DMF) mixtures.

After the desired amino acid sequence has been completed, the desired peptide is decoupled from the resin support by treatment with a reagent, such as TFA or hydrogen fluoride (HF), which not only cleaves the peptide from the resin, but also cleaves all remaining side chain protecting groups. When the chloromethylated resin is used, HF treatment results in the formation of the free peptide acids. When the benzhydrylamine resin is used, HF treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These and other solid support peptide synthesis procedures are well-known in the art. Such procedures are also described by Stewart and Young in Solid support Peptide Syntheses (2nd Ed., Pierce Chemical Company, 1984).

b. Recombinant Production

A polypeptide, such as a monoclonal antibody (or a fragment thereof) which specifically binds analyte (or fragments thereof), can be recombinantly produced using methods known in the art. For example, an isolated nucleic acid comprising a nucleotide sequence encoding the antibody (or a fragment thereof) can be expressed in a host cell, and the antibody can be isolated. The isolated nucleic acid comprises a nucleotide sequence encoding the amino acid sequence of the antibody against analyte. The isolated nucleic acid can be synthesized with an oligonucleotide synthesizer, for example. One of ordinary skill in the art will readily appreciate that, due to the degeneracy of the genetic code, more than one nucleotide sequence can encode a given amino acid sequence. In this regard, a nucleotide sequence encoding an amino acid sequence that is substantially identical to that of the antibody against analyte can be used, provided that the variant antibody as expressed competes with the antibody against the analyte. Codons, which are favored by a given host cell, preferably are selected for recombinant production. A nucleotide sequence encoding the amino acid sequence of the antibody against the analyte can be combined with other nucleotide sequences using polymerase chain reaction (PCR), ligation, or ligation chain reaction (LCR) to encode an anti-analyte antibody or antigenically reactive fragment thereof. The individual oligonucleotides typically contain 5' or 3' overhangs for complementary assembly. Once assembled, the nucleotide sequence encoding an anti-analyte antibody or antigenically reactive fragment thereof can be inserted into a vector, operably linked to control sequences as necessary for expression in a given host cell, and introduced (such as by transformation or transfection) into a host cell. The nucleotide sequence can be further manipulated (for example, linked to one or more nucleotide sequences encoding additional immunoglobulin domains, such as additional constant regions) and/or expressed in a host cell.

Although not all vectors and expression control sequences may function equally well to express a polynucleotide sequence of interest and not all hosts function equally well with the same expression system, it is believed that those skilled in the art will be able to make a selection among these vectors, expression control sequences, optimized codons, and hosts for use in the present disclosure without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, should also be considered. In selecting an expression control sequence, a variety of factors also can be considered. These include, but are not limited to, the relative strength of the sequence, its controllability, and its compatibility with the nucleotide sequence encoding the anti-analyte antibody, particularly with regard to potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products encoded by the nucleotide sequence, etc.

The recombinant vector can be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

The vector is preferably an expression vector in which the polynucleotide sequence encoding the anti-analyte antibody is operably linked to additional segments required for transcription of the polynucleotide sequence. The vector is typically derived from plasmid or viral DNA. A number of suitable expression vectors for expression in the host cells mentioned herein are commercially available or described in the literature. Useful expression vectors for eukaryotic hosts, include, but are not limited to, vectors comprising expression control sequences from SV40, bovine papilloma virus, adenovirus and cytomegalovirus. Specific vectors include pCDNA3.1 (+)\Hyg (Invitrogen Corp., Carlsbad, Calif.) and pCI-neo (Stratagene, La Jolla, Calif.). Examples of expression vectors for use in yeast cells include, but are not limited to, the 2µ plasmid and derivatives thereof, the POT1 vector (see, e.g., U.S. Pat. No. 4,931,373), the pJSO37 vector (described in Okkels, Ann. New York Acad. Sci. 782: 202-207 (1996)) and pPICZ A, B or C (Invitrogen). Examples of expression vectors for use in insect cells include, but are not limited to, pVL941, pBG311 (Cate et al., Cell 45: 685-698 (1986)), and pBluebac 4.5 and pMelbac (both of which are available from Invitrogen).

Other vectors that can be used allow the nucleotide sequence encoding the anti-analyte antibody to be amplified in copy number. Such amplifiable vectors are well-known in the art. These vectors include, but are not limited to, those vectors that can be amplified by dihydrofolate reductase (DHFR) amplification (see, for example, Kaufinan, U.S. Pat. No. 4,470,461; and Kaufinan et al., Mol. Cell. Biol. 2: 1304-1319 (1982)) and glutamine synthetase (GS) amplification (see, for example, U.S. Pat. No. 5,122,464 and European Pat. App. Pub. No. 0 338 841).

The recombinant vector can further comprise a nucleotide sequence enabling the vector to replicate in the host cell in question. An example of such a sequence for use in a mammalian host cell is the SV40 origin of replication. Suitable sequences enabling the vector to replicate in a yeast cell are the yeast plasmid 2µ replication genes REP 1-3 and origin of replication.

The vector can also comprise a selectable marker, namely, a gene or polynucleotide, the product of which complements a defect in the host cell, such as the gene coding for DHFR or the *Schizosaccharomyces pombe* TPI gene (see, e.g., Russell, Gene 40: 125-130 (1985)), or one which confers resistance to a drug, such as ampicillin, kanamycin, tetracycline, chloramphenicol, neomycin, hygromycin or methotrexate. For filamentous fungi, selectable markers include, but are not limited to, amdS, pyrG, arcB, niaD and sC.

Also present in the vector are "control sequences," which are any components that are necessary or advantageous for the expression of the anti-analyte antibody. Each control sequence can be native or foreign to the nucleotide sequence encoding the anti-analyte antibody. Such control sequences include, but are not limited to, a leader, a polyadenylation sequence, a propeptide sequence, a promoter, an enhancer or an upstream activating sequence, a signal peptide sequence, and a transcription terminator. At a minimum, the control sequences include at least one promoter operably linked to the polynucleotide sequence encoding the anti-analyte antibody.

By "operably linked" is meant the covalent joining of two or more nucleotide sequences, by means of enzymatic ligation or otherwise, in a configuration relative to one another such that the normal function of the sequences can be performed. For example, a nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in the same reading frame. Linking is accomplished by ligation at convenient restriction sites. If such sites do not exist, then synthetic oligonucleotide adaptors or linkers can be used, in conjunction with standard recombinant DNA methods.

A wide variety of expression control sequences can be used in the context of the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, J. Mol. Biol. 196: 947-50 (1987)).

In order to improve expression in mammalian cells a synthetic intron can be inserted in the 5' untranslated region of a polynucleotide sequence encoding the antibody or a fragment thereof. An example of a synthetic intron is the synthetic intron from the plasmid pCI-Neo (available from Promega Corporation, Madison, Wis.).

Examples of suitable control sequences for directing transcription in insect cells include, but are not limited to, the polyhedrin promoter, the P10 promoter, the baculovirus immediate early gene 1 promoter, the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator, and the ADH3 terminator.

The polynucleotide sequence encoding the antibody of interest may or may not also include a polynucleotide sequence that encodes a signal peptide. The signal peptide is present when the anti-analyte antibody is to be secreted from the cells in which it is expressed. Such signal peptide, if present, should be one recognized by the cell chosen for expression of the polypeptide. The signal peptide can be homologous or heterologous to the anti-analyte monoclonal antibody or can be homologous or heterologous to the host cell, i.e., a signal peptide normally expressed from the host cell or one which is not normally expressed from the host cell. Accordingly, the signal peptide can be prokaryotic, for example, derived from a bacterium, or eukaryotic, for example, derived from a mammalian, insect, filamentous fungal, or yeast cell.

The presence or absence of a signal peptide will, for example, depend on the expression host cell used for the production of the anti-analyte antibody. For use in filamentous fungi, the signal peptide can conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide can be derived from an insect gene (see, e.g., Int'l Pat. App. Pub. No. WO 90/05783), such as the lepidopteran *Manduca sexta* adipokinetic hormone precursor (see, e.g., U.S. Pat. No. 5,023,328), the honeybee melittin (Invitrogen), ecdysteroid UDP glucosyltransferase (egt) (Murphy et al., Protein Expression and Purification 4: 349-357 (1993), or human pancreatic lipase (hpl) (Methods in Enzymology 284: 262-272 (1997)).

Specific examples of signal peptides for use in mammalian cells include murine Ig kappa light chain signal peptide (Coloma, J. Imm. Methods 152: 89-104 (1992)). Suitable signal peptides for use in yeast cells include the α-factor signal peptide from *S. cerevisiae* (see, e.g., U.S. Pat. No. 4,870,008), the signal peptide of mouse salivary amylase (see, e.g., Hagenbuchle et al., Nature 289: 643-646 (1981)), a modified carboxypeptidase signal peptide (see, e.g., Valls et al., Cell 48: 887-897 (1987)), the yeast BAR1 signal peptide (see, e.g., Int'l Pat. App. Pub. No. WO 87/02670), and the yeast aspartic protease 3 (YAP3) signal peptide (see, e.g., Egel-Mitani et al., Yeast 6: 127-137 (1990)).

Any suitable host can be used to produce the anti-analyte antibody, including bacteria, fungi (including yeasts), plant, insect, mammal or other appropriate animal cells or cell lines, as well as transgenic animals or plants. Examples of bacterial host cells include, but are not limited to, gram-positive bacteria, such as strains of *Bacillus*, for example, *B. brevis* or *B. subtilis, Pseudomonas* or *Streptomyces*, or gram-negative bacteria, such as strains of *E. coli*. The introduction of a vector into a bacterial host cell can, for instance, be effected by protoplast transformation (see, for example, Chang et al., Molec. Gen. Genet. 168: 111-115 (1979)), using competent cells (see, for example, Young et al., J. of Bacteriology 81: 823-829 (1961), or Dubnau et al., J. of Molec. Biol. 56: 209-221 (1971)), electroporation (see, for example, Shigekawa et al., Biotechniques 6: 742-751 (1988)), or conjugation (see, for example, Koehler et al., J. of Bacteriology 169: 5771-5278 (1987)).

Examples of suitable filamentous fungal host cells include, but are not limited to, strains of *Aspergillus*, for example, *A. oryzae, A. niger*, or *A. nidulans, Fusarium* or *Trichoderma*. Fungal cells can be transformed by a process involving protoplast formation, transformation of the protoplasts, and regeneration of the cell wall using techniques known to those ordinarily skilled in the art. Suitable procedures for transformation of *Aspergillus* host cells are described in European Pat. App. Pub. No. 238 023 and U.S. Pat. No. 5,679,543. Suitable methods for transforming *Fusarium* species are described by Malardier et al., Gene 78: 147-156 (1989), and Int'l Pat. App. Pub. No. WO 96/00787. Yeast can be transformed using the procedures described by Becker and Guarente, In Abelson, J. N. and Simon, M. I., editors, Guide to Yeast Genetics and Molecular Biology, Methods in Enzymology 194: 182-187, Academic Press, Inc., New York; Ito et al, J. of Bacteriology 153: 163 (1983); and Hinnen et al., PNAS USA 75: 1920 (1978).

Examples of suitable yeast host cells include strains of *Saccharomyces*, for example, *S. cerevisiae*, *Schizosaccharomyces*, *Klyveromyces*, *Pichia*, such as *P. pastoris* or *P. methanolica*, *Hansenula*, such as *H. polymorpha* or *yarrowia*. Methods for transforming yeast cells with heterologous polynucleotides and producing heterologous polypeptides therefrom are disclosed by Clontech Laboratories, Inc, Palo Alto, Calif., USA (in the product protocol for the Yeastmaker™ Yeast Transformation System Kit), and by Reeves et al., FEMS Microbiology Letters 99: 193-198 (1992), Manivasakam et al., Nucleic Acids Research 21: 4414-4415 (1993), and Ganeva et al., FEMS Microbiology Letters 121: 159-164 (1994).

Examples of suitable insect host cells include, but are not limited to, a Lepidoptora cell line, such as *Spodoptera frugiperda* (Sf9 or Sf21) or *Trichoplusia ni* cells (High Five) (see, e.g., U.S. Pat. No. 5,077,214). Transformation of insect cells and production of heterologous polypeptides are well-known to those skilled in the art.

Examples of suitable mammalian host cells include Chinese hamster ovary (CHO) cell lines, simian (e.g., Green Monkey) cell lines (COS), mouse cells (for example, NS/O), baby hamster kidney (BHK) cell lines, human cells (such as human embryonic kidney (HEK) cells (e.g., HEK 293 cells (A.T.C.C. Accession No. CRL-1573))), myeloma cells that do not otherwise produce immunoglobulin protein, and plant cells in tissue culture. Preferably, the mammalian host cells are CHO cell lines and HEK 293 cell lines. Another host cell is the B3.2 cell line (e.g., Abbott Laboratories, Abbott Bioresearch Center), or another dihydrofolate reductase deficient (DHFR-) CHO cell line (e.g., available from Invitrogen).

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamine™ 2000. These methods are well-known in the art and are described, for example, by Ausbel et al. (eds.), Current Protocols in Molecular Biology, John Wiley & Sons, New York, USA (1996). The cultivation of mammalian cells is conducted according to established methods, e.g., as disclosed in Jenkins, Ed., Animal Cell Biotechnology, Methods and Protocols, Human Press Inc. Totowa, N.J., USA (1999), and Harrison and Rae, General Techniques of Cell Culture, Cambridge University Press (1997).

In the production methods, cells are cultivated in a nutrient medium suitable for production of the anti-analyte antibody using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the anti-human analyte monoclonal antibody to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the anti-analyte antibody is secreted into the nutrient medium, it can be recovered directly from the medium. If the anti-analyte antibody is not secreted, it can be recovered from cell lysates.

The resulting anti-analyte antibody can be recovered by methods known in the art. For example, the anti-analyte antibody can be recovered from the nutrient medium by conventional procedures including, but not limited to, centrifugation, filtration, extraction, spray drying, evaporation, or precipitation.

The anti-analyte antibody can be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (see, for example, Janson and Ryden, editors, Protein Purification, VCH Publishers, New York (1989)).

c. Antibody Production by Immunization, Hybridomas or Other Means

Other antibodies (or fragments thereof) that specifically bind to analyte (or fragments thereof) can be made using a variety of different techniques known in the art. For example, polyclonal and monoclonal antibodies can be raised by immunizing a suitable subject (such as, but not limited to, a rabbit, a goat, a mouse, or other mammal) with an immunogenic preparation, which contains a suitable immunogen. The immunogen can be enriched/purified and isolated from a cell that produces it using affinity chromatography, immune-precipitation or other techniques, which are well-known in the art. Alternatively, immunogen can be prepared using chemical synthesis using routine techniques known in the art (such as, but not limited to, a synthesizer). The antibodies raised in the subject can then be screened to determine if the antibodies bind to the immunogen (or a fragment thereof).

The unit dose of immunogen (namely, the purified protein, tumor cell expressing the protein, or recombinantly expressed immunogen (or a fragment or a variant (or a fragment thereof) thereof) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen.

Other methods of raising antibodies include using transgenic mice, which express human immunoglobin genes (see, for example, Intl Pat. App. Pub. Nos. WO 91/00906, WO 91/10741, and WO 92/03918). Alternatively, human monoclonal antibodies can be produced by introducing an antigen into immune-deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (see, for example, Int'l Pat. App. Pub. No. WO 93/05796; U.S. Pat. No. 5,411,749; or McCune et al., Science 241: 1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody-producing cells can be harvested from an immunized animal and used to prepare monoclonal antibodies using standard techniques. For example, the antibody-producing cells can be fused by standard somatic cell fusion procedures with immortalizing cells, such as myeloma cells, to yield hybridoma cells. Such techniques are well-known in the art, and include, for example, the hybridoma technique as originally developed by Kohler and Milstein, Nature 256: 495-497 (1975)), the human B cell hybridoma technique (Kozbar et al., Immunology Today 4: 72 (1983)), and the Epstein-Barr virus (EBV)-hybridoma technique to produce human monoclonal antibodies (Cole et al., Monoclonal Antibodies and Cancer Therapy, Alan R. Liss, Inc. pp. 77-96 (1985)). The technology for producing monoclonal antibody hybridomas is well-known to those skilled in the art.

Monoclonal antibodies also can be made by harvesting antibody-producing cells, for example, splenocytes, from transgenic mice, which express human immunoglobulin genes and which have been immunized with the immunogen. The splenocytes can be immortalized through fusion with human myelomas or through transformation with EBV. These hybridomas can be made using human B cell- or EBV-hybridoma techniques described in the art (See, for example, Boyle et al., European Pat. Pub. No. 0 614 984).

Hybridoma cells producing a monoclonal antibody, which specifically binds to the immunogen, are detected by screening the hybridoma culture supernatants by, for example, screening to select antibodies that specifically bind to the immobilized immunogen (or a fragment thereof), or by testing the antibodies as described herein to determine if the antibodies have the desired characteristics, namely, the ability to bind to immunogen (or a fragment thereof). After hybridoma cells are identified that produce antibodies of the desired specificity, the clones may be subcloned, e.g., by limiting dilution procedures, for example the procedure described by Wands et al. (Gastroenterology 80: 225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in Monoclonal Antibodies: A New Dimension In Biological Analyses, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the immunogen or a fragment thereof. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD1 available from Invitrogen). Briefly, the antibody library is screened to identify and isolate phages or yeast cells that express an antibody that specifically binds to the immunogen or a fragment thereof. Preferably, the primary screening of the library involves screening with an immobilized immunogen or a fragment thereof.

Following screening, the display phage or yeast is isolated and the polynucleotide encoding the selected antibody can be recovered from the display phage or yeast (for example, from the phage or yeast genome) and subcloned into other expression vectors (e.g., into *Saccharomyces cerevesiae* cells, for example EBY100 cells (Invitrogen)) by well-known recombinant DNA techniques. The polynucleotide can be further manipulated (for example, linked to nucleic acid encoding additional immunoglobulin domains, such as additional constant regions) and/or expressed in a host cell.

Once a monoclonal antibody that specifically binds to analyte is obtained in accordance with methods described above, it can be sequenced in accordance with methods known in the art. The antibody then can be made using recombinant DNA technology, chemical synthesis, or a combination of chemical synthesis and recombinant DNA technology as described above.

Furthermore, in some aspects of the disclosure, it may be possible to employ commercially available anti-analyte antibodies or methods for production of anti-analyte antibodies as described in the literature. Alternatively, anti-analyte antibodies can be produced using methods described in the literature.

d. Antibody Fragments

An antigenically reactive fragment of an antibody that binds to analyte also can be used as described herein. The antibody fragment can be a Fab, a Fab', a Fab'-SH fragment, a di-sulfide linked Fv, a single chain Fv (scFv), a F(ab')2 fragment, and the like. Various techniques are known to those skilled in the art for the production of antibody fragments. For example, such fragments can be derived via proteolytic digestion of intact antibodies (see, for example, Morimoto et al., J. Biochem. Biophys. Methods 24: 107-117 (1992), and Brennan et al., Science 229: 81 (1985)) or produced directly by recombinant host cells. For example, Fab'-SH fragments can be directly recovered from *E. coli* and chemically coupled to form F(ab')2 fragments (see, e.g., Carter et al., Bio/Technology 10: 163-167 (1992)). In another embodiment, the F(ab')2 is formed using the leucine zipper GCN4 to promote assembly of the F(ab')2 molecule. Alternatively, Fv, Fab or F(ab')2 fragments can be isolated directly from recombinant host cell culture. Single chain variable region fragments (scFv) are made by linking light and/or heavy chain variable regions by using a short linking peptide or sequence (see, e.g., Bird et al., Science 242: 423-426 (1998)). The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art. Moreover, other forms of single-chain antibodies, such as diabodies are also contemplated by the present disclosure. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see, for example, Holliger et al., PNAS USA 90: 6444-6448 (1993); and Poljak et al., Structure 2: 1121-1123 (1994)).

The antibody and antigenically reactive fragment thereof have a variety of uses. In one aspect, the antibody (or a fragment thereof) can be used as one or more immunodiagnostic reagents. For example, the antibodies can be used as one or more immunodiagnostic reagents in one or more methods for detecting the presence of analyte in a test sample. More specifically, the antibody (or antigenically reactive fragment thereof) can be used as a capture antibody or a detection antibody in an assay to detect the presence of analyte in a test sample.

The following examples serve to illustrate the present disclosure. The examples are not intended to limit the scope of the claimed invention in any way.

Example 1

The assay range of currently marketed PSA assays is approximately from 0.1 ng/mL to 100 ng/mL (e.g., Abbott ARCHITECT® Total PSA Assay, Abbott Park, Ill.). At higher PSA concentrations, a hook effect can be observed in a one-step assay format. In the present example, we modeled the signal response of analyte concentration from 0 to 400,000 ng/mL in the one-step assay format conducted as described herein in order to expand the assay dynamic range for detecting PSA.

For modeling conditions, Antibody 1 was coated on type 1 microparticles with a final antibody concentration of 10 nM, and dissociation constant to PSA of 0.5 nM. Antibody 2 was coated on type 2 microparticles with a final antibody concentration is 10 nM, and dissociation constant to PSA of 50 nM. The conjugate antibody concentration was 10 nM and its dissociation constant to PSA was 0.5 nM. The amount of conjugate antibody bound to each microparticles type was determined by first calculating the amount of analyte bound to the microparticles using the standard binding equations. Then, the percentage of analyte on the microparticles able to bind to conjugate antibody was calculated. Table 1 lists the amount of analyte detected on each type of microparticle.

TABLE 1

| ng/mL | Signal from Type 1 microparticles | Signal from Type 2 microparticles | Ratio of # 2/# 1 |
|---|---|---|---|
| 0.00 | 0.000 | 0.000 | 0.000 |
| 0.05 | 0.001 | 0.000 | 0.010 |
| 0.10 | 0.003 | 0.000 | 0.010 |
| 5 | 0.141 | 0.001 | 0.010 |
| 50 | 1.402 | 0.016 | 0.012 |
| 100 | 2.770 | 0.038 | 0.014 |
| 200 | 5.319 | 0.112 | 0.021 |
| 400 | 7.113 | 0.459 | 0.065 |
| 800 | 4.005 | 0.828 | 0.207 |
| 1,600 | 2.053 | 0.845 | 0.411 |
| 3,200 | 1.035 | 0.641 | 0.619 |
| 6,400 | 0.519 | 0.405 | 0.779 |

TABLE 1-continued

| ng/mL | Signal from Type 1 microparticles | Signal from Type 2 microparticles | Ratio of # 2/# 1 |
|---|---|---|---|
| 12,800 | 0.260 | 0.229 | 0.881 |
| 25,600 | 0.130 | 0.122 | 0.938 |
| 51,200 | 0.065 | 0.063 | 0.968 |
| 102,400 | 0.033 | 0.032 | 0.984 |
| 204,800 | 0.016 | 0.016 | 0.992 |
| 409,600 | 0.008 | 0.008 | 0.996 |

Table 1 provides illustrative data showing the expansion of dynamic range for determining the concentration of a representative analyte (here, PSA) in a test sample. The values in column 2 can be used to determine PSA concentration. The assay dynamic range is from 0.05 ng/mL to 409,600 ng/mL, as compared with the currently marketed ARCHITECT® PSA assay range which is from 0.1 ng/mL to 100 ng/mL.

Figure 7A:
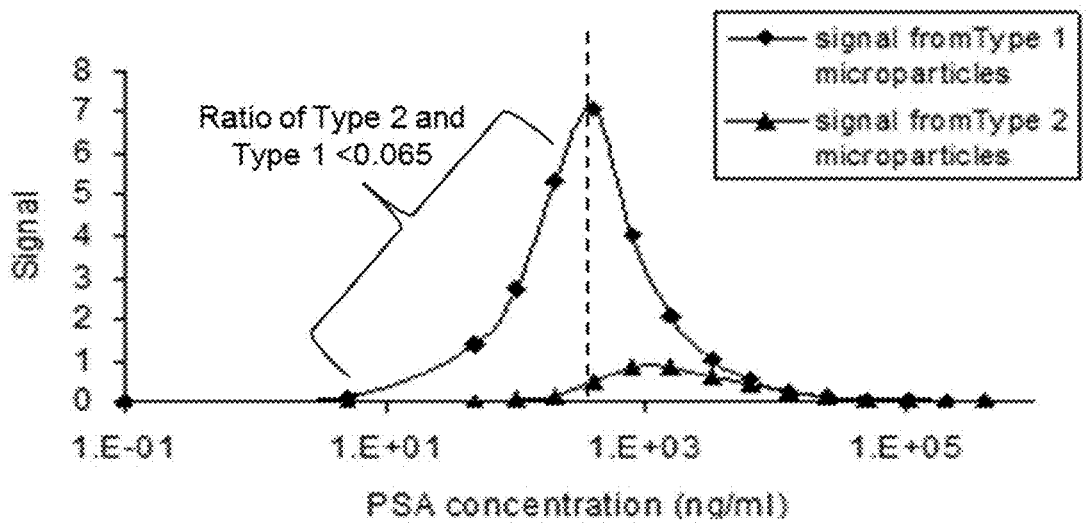
FIGS. 7A-B provide an example of a modeled sandwich assay for Prostate-specific antigen (PSA).
Figure 7B:
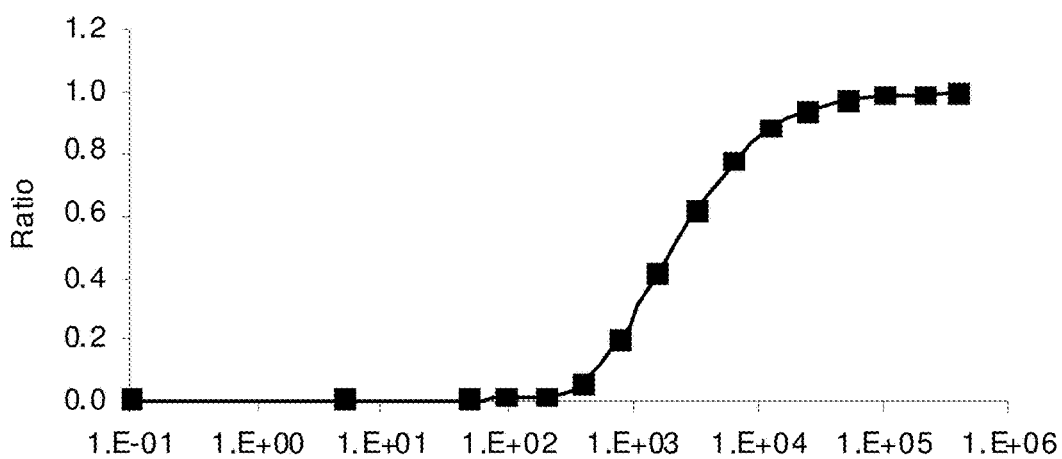

Table 1 and FIG. 7 provide illustrative data showing the expansion of dynamic range to determine the concentration of a representative analyte (here, PSA) in a test sample. The signal from Type 1 microparticles reaches its maximum intensity at 400 ng/mL analyte concentration and decreases at higher analyte concentrations. Therefore, each signal value corresponds to two analyte concentrations. If this intensity plot is used as a calibration curve, it is impossible to determine the concentration of the test sample. However, the signal ratio of Type 2 microparticle and Type 1 microparticle monotonically increases as a function of analyte concentration. One of the ratios thus can be used as a flag or indicator. For example, at maximum signal from Type 1 microparticle, the signal ratio is 0.065. Thus, the signal ratio of 0.065 will be the flag value. If the signal ratio for a test sample is less than 0.065, then the rising section of the signal plot from Type 1 microparticle will be used for calibration (identified on FIG. 7); if the signal ratio is higher than 0.065, then the sinking section of the signal plot from Type 1 microparticle will be used for calibration. The model confirms that the assay dynamic range can be extended to 409,600 ng/mL, if not higher. This is accomplished by including a high and low affinity antibody in the assay and using the signal ratio as a flag value to choose which section of the calibration curve to use for calibration. The flag value can also be used to determine if the result from the Type 1 curve is falsely decreased due to a hook effect caused by a high concentration of PSA in the sample.

Example 2

Provided herein is an example of a sandwich assay using two detection antibodies in a one-step assay format.

This assay was designed to measure the concentration of a brain natriuretic peptide (cyclic peptide; BNP) using affinity maturated antibodies (Abbott Laboratories, Abbott Park, Ill.; e.g., produced as described in U.S. Pat. No. 7,939,069, incorporated by reference for its teachings regarding same) capable of detecting the peptide in a sandwich assay.

The assay is performed in one-step sandwich format. The capture antibody was coated on 5 micron Polymer Lab (Church Stretton, United Kingdom) particles. Two antibodies, one high affinity and one low affinity, were labeled with Cy3 and FITC fluorescent dye, respectively. The high affinity antibody (Ab1-Cy3) has a $K_D$ for BNP of 0.3 nM. The low affinity antibody (Ab2-FITC) has a $K_D$ for BNP greater than 20 nM.

100 μL of analyte at concentrations ranging from 250 nM to 2 pM were sequentially mixed with 5 μL 100 nM Ab1-Cy3, 2 μL 0.1% microparticles, and 10 μL 400 nM Ab2-FITC. The microparticles were washed after one hour of incubation and imaged on a microscope. The analytes detected by Ab1-Cy3 were measured in the Cy3 channel, and the analytes detected by Ab2-FITC were measured in the FITC channel.

Figure 8A:
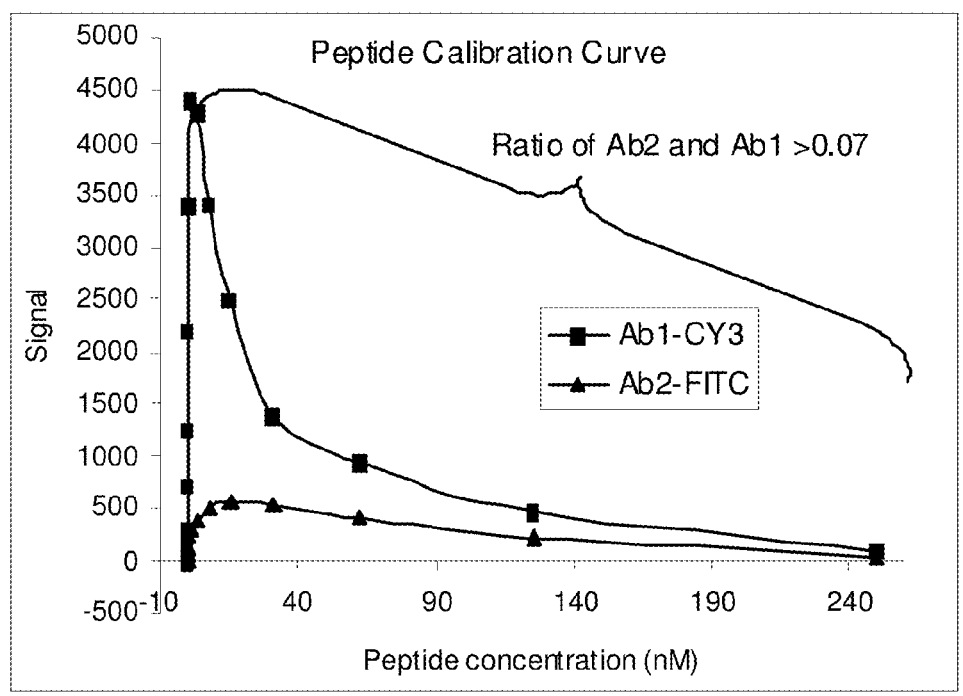
FIGS. 8A-B provide an example of a sandwich assay for brain natriuretic peptide (BNP).
Figure 8B:
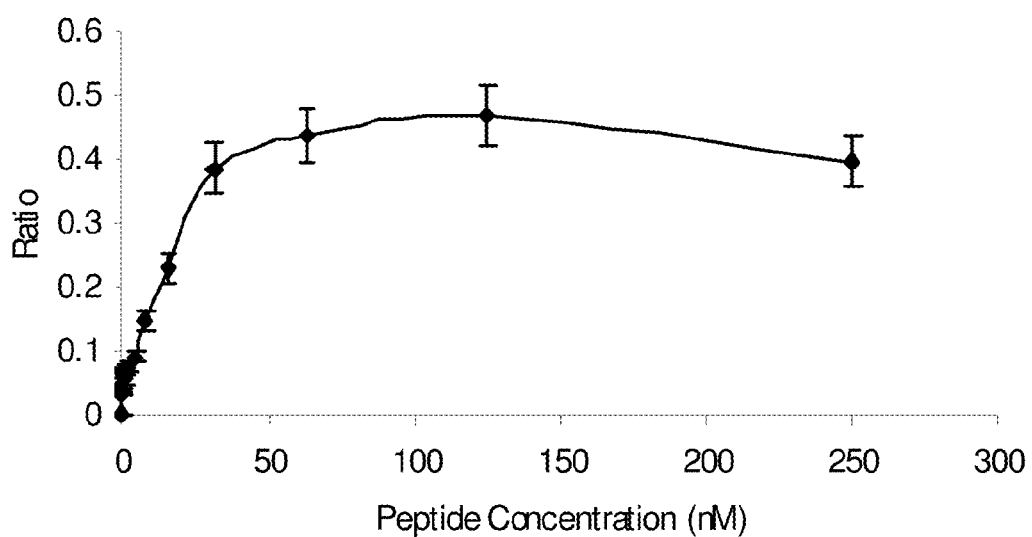

FIG. 8a shows the signal plot of peptide from 2 pM to 250 nM measured independently in the Cy3 and FITC channels. A hook effect was observed using data from both channels. FIG. 8b shows the ratio plot of FITC and Cy3 channel as a function of the peptide concentration; it increases monotonically with analyte concentration. At a maximum Cy3 signal, the signal ratio is 0.07, which is used as the flag value. If the signal ratio for a test signal is higher than 0.07, then the calibration plot in the identified area of FIG. 8a is used to determine its concentration.

All patents, patent application publications, journal articles, textbooks, and other publications mentioned in the specification are indicative of the level of skill of those in the art to which the disclosure pertains.

The commonly owned, co-pending application U.S. Nonprovisional application Ser. No. 13/833,365, entitled "ASSAY WITH INTERNAL CALIBRATION," filed on Mar. 15, 2013 is explicitly incorporated by reference in its entirety for its teachings regarding kits and methods for assays having a single internal calibrator.

All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A method of expanding the dynamic range of an assay, comprising:
   a) contacting a test sample suspected of comprising an analyte with a tracer comprising said analyte or fragment thereof attached to a label, a first analyte-binding molecule attached to a first solid support, a second analyte-binding molecule attached to a second solid support, wherein the binding affinity for the analyte of the first analyte-binding molecule is greater than that of the second analyte-binding molecule, wherein the first analyte-binding molecule and the second analyte-binding molecule do not concurrently bind to the analyte;
   b) measuring the signal intensities from the tracer bound to the first analyte-binding molecule on the first solid support and the second analyte-binding molecule on the second solid support; and
   c) establishing a flag value at or near the leveling off value (plateau) of the signal intensity of the tracer bound to the first analyte-binding protein attached to the first solid support wherein the flag value is a threshold or cut-off value that governs whether the signal from the analyte-binding molecule with relatively higher binding affinity for the analyte is used in determining the concentration of analyte in a test sample.

2. The method of claim 1, wherein when the signal intensity of the tracer bound to the first analyte-binding protein attached to the first solid support is equal to or less than the flag value, then the signal intensity of the tracer bound to the second analyte-binding protein attached to the second solid support is used to determine analyte concentration.

3. The method of claim 1, wherein one or more of the first analyte-binding molecule and/or the second analyte-binding molecule is an antibody or fragment thereof.

4. The method of claim 1, wherein the label is selected from the group consisting of an enzyme, a chromophore, and a fluorophore.

5. The method of claim 1, wherein the first solid support and the second solid support are independently selected from the group consisting of a particle, a microparticle, a bead, an electrode and a multiwell plate.

6. The method of claim 1, wherein the first solid support is a microparticle or bead comprising a first chromophore and the second solid support is a microparticle or bead comprising a second chromophore.

7. The method of claim 1, wherein the first solid support and the second solid support are microparticles which differ in either shape or size.

8. The method of claim 1, wherein the first solid support and the second solid support are different.

9. The method of claim 1, wherein the first solid support is a first electrode and the second solid support is a second electrode, wherein the first electrode and the second electrode are spatially separated.

10. The method of claim 1, wherein the difference in binding affinity of the first analyte-binding molecule and the second analyte-binding molecule for the analyte ranges from about 5-fold to about 100-fold.

11. The method of claim 1, wherein the difference in binding affinity of the first analyte-binding molecule and the second analyte-binding molecule for the analyte is at least about 100-fold.

* * * * *